United States Patent [19]
Yasukawa et al.

[11] Patent Number: 5,766,132
[45] Date of Patent: Jun. 16, 1998

[54] WRIST-WORN PORTABLE DEVICE AND A WRIST-WORN PULSE WAVE MEASURING DEVICE

[75] Inventors: Naoaki Yasukawa; Motomu Hayakawa, both of Suwa; Chiaki Nakamura, Chiba, all of Japan

[73] Assignees: Seiko Epson Corporation, Tokyo; Seiko Instruments, Inc., Chiba-ken, both of Japan

[21] Appl. No.: 672,466

[22] Filed: Jun. 26, 1996

[30] Foreign Application Priority Data

Jun. 30, 1995 [JP] Japan .................. 7-166551
Jun. 5, 1996 [JP] Japan .................. 8-143341

[51] Int. Cl.⁶ .................................................. A61B 5/02
[52] U.S. Cl. ...................... 600/503; 600/500; 600/502
[58] Field of Search .................................. 128/690, 687, 128/689, 633; 600/503, 500, 502, 310

[56] References Cited

U.S. PATENT DOCUMENTS

| | | | |
|---|---|---|---|
| 3,972,320 | 8/1976 | Kalman | 128/690 |
| 4,305,401 | 12/1981 | Reissmueller et al. | 128/690 |
| 4,802,488 | 2/1989 | Eckerle | 128/690 |
| 4,863,265 | 9/1989 | Flower et al. | 128/633 |
| 5,197,489 | 3/1993 | Conlan | 128/690 |
| 5,301,154 | 4/1994 | Suga | 128/690 |

FOREIGN PATENT DOCUMENTS

| | | |
|---|---|---|
| 0 542 413 | 5/1993 | European Pat. Off. . |
| 0 653 182 | 5/1995 | European Pat. Off. . |
| 2 579 791 | 10/1986 | France . |
| 2 583 282 | 12/1986 | France . |
| 89/05116 | 6/1989 | WIPO . |
| 94/13198 | 6/1994 | WIPO . |

*Primary Examiner*—Lee S. Cohen
*Assistant Examiner*—Stephen Huang
*Attorney, Agent, or Firm*—W. Glen Johnson; Eric B. Janofsky

[57] ABSTRACT

The invention provides a wrist-worn pulse wave measuring device capable of outputting data measured by the wrist-worn pulse wave measuring device to an external data processing device without using a large device body. In the pulse information processing apparatus, a connector piece of a sensor unit is mounted to a connector of a wrist-worn pulse wave measuring device when measuring the pulse. A data transmission connector piece is mounted to the connector of the pulse wave measuring device when transmitting data with a data processor. Whether the operating mode is the pulse measurement mode or the data transmission mode is determined by a signal discriminator which discriminates the signal input from the connector of the pulse wave measuring device.

10 Claims, 20 Drawing Sheets

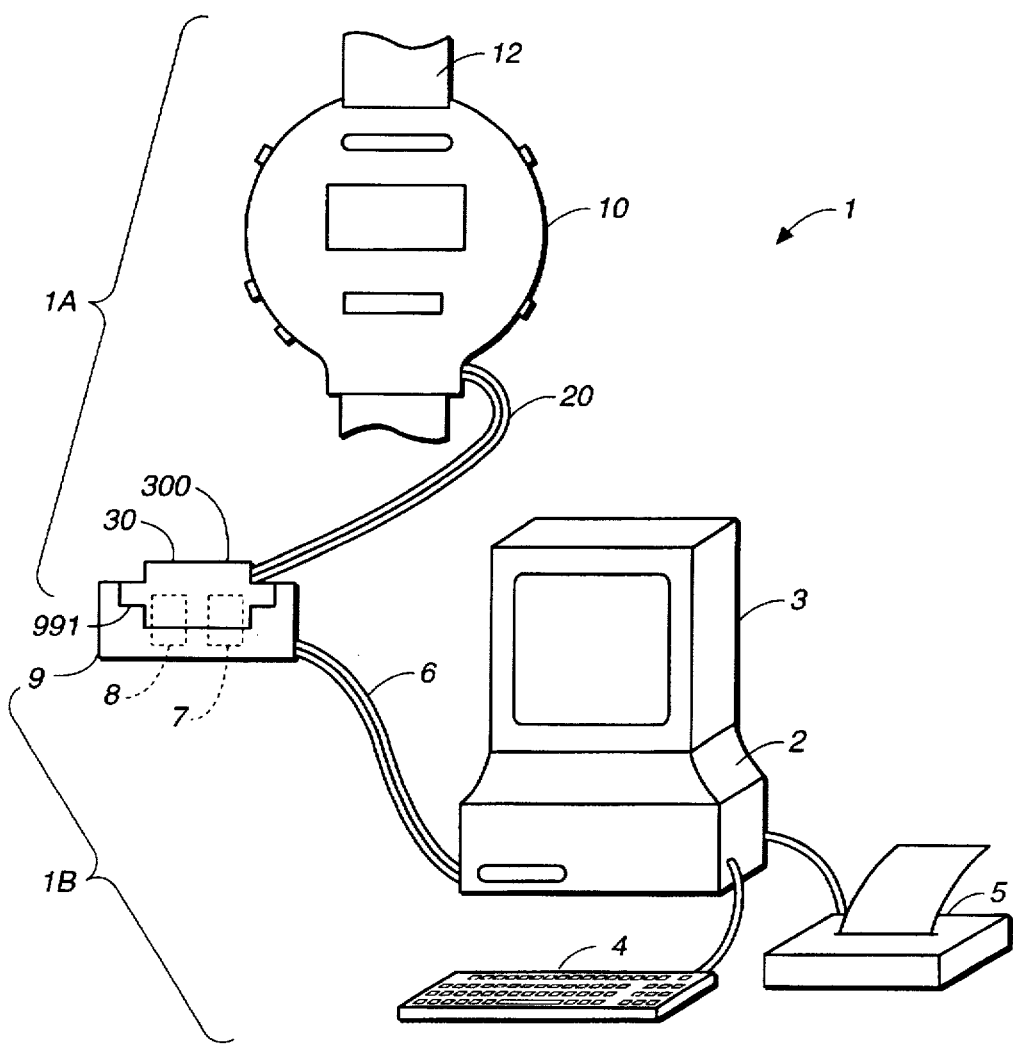
FIG._1

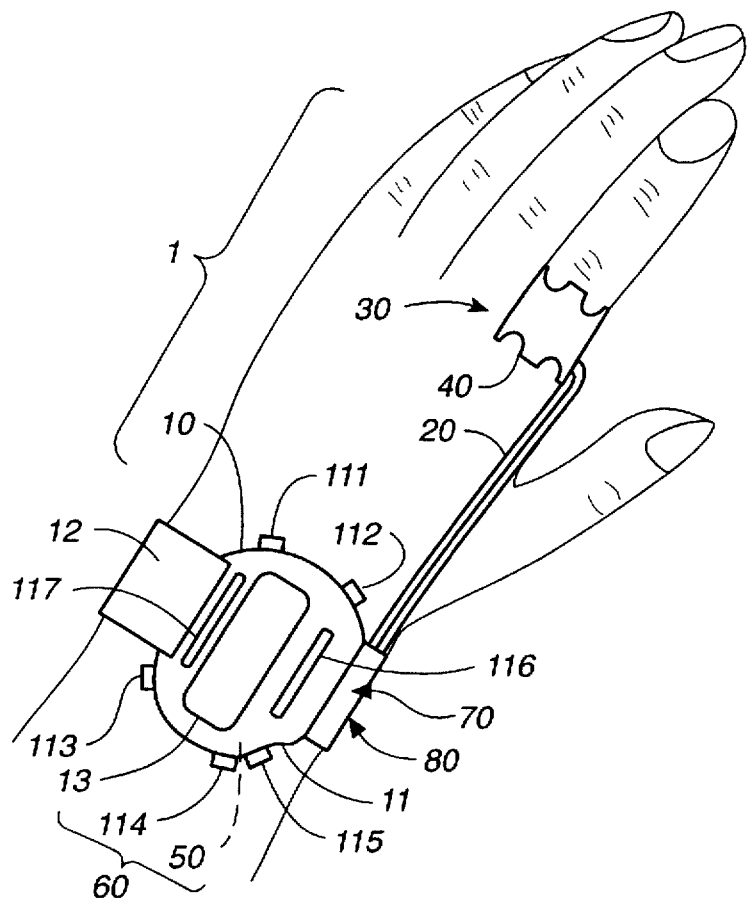
FIG._2A
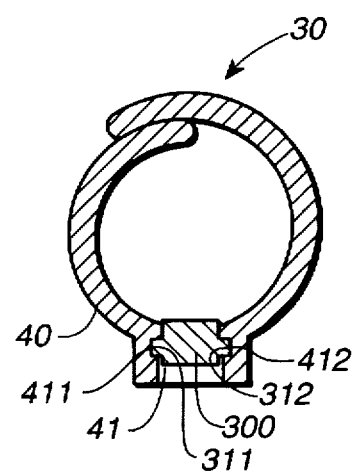
FIG._2B

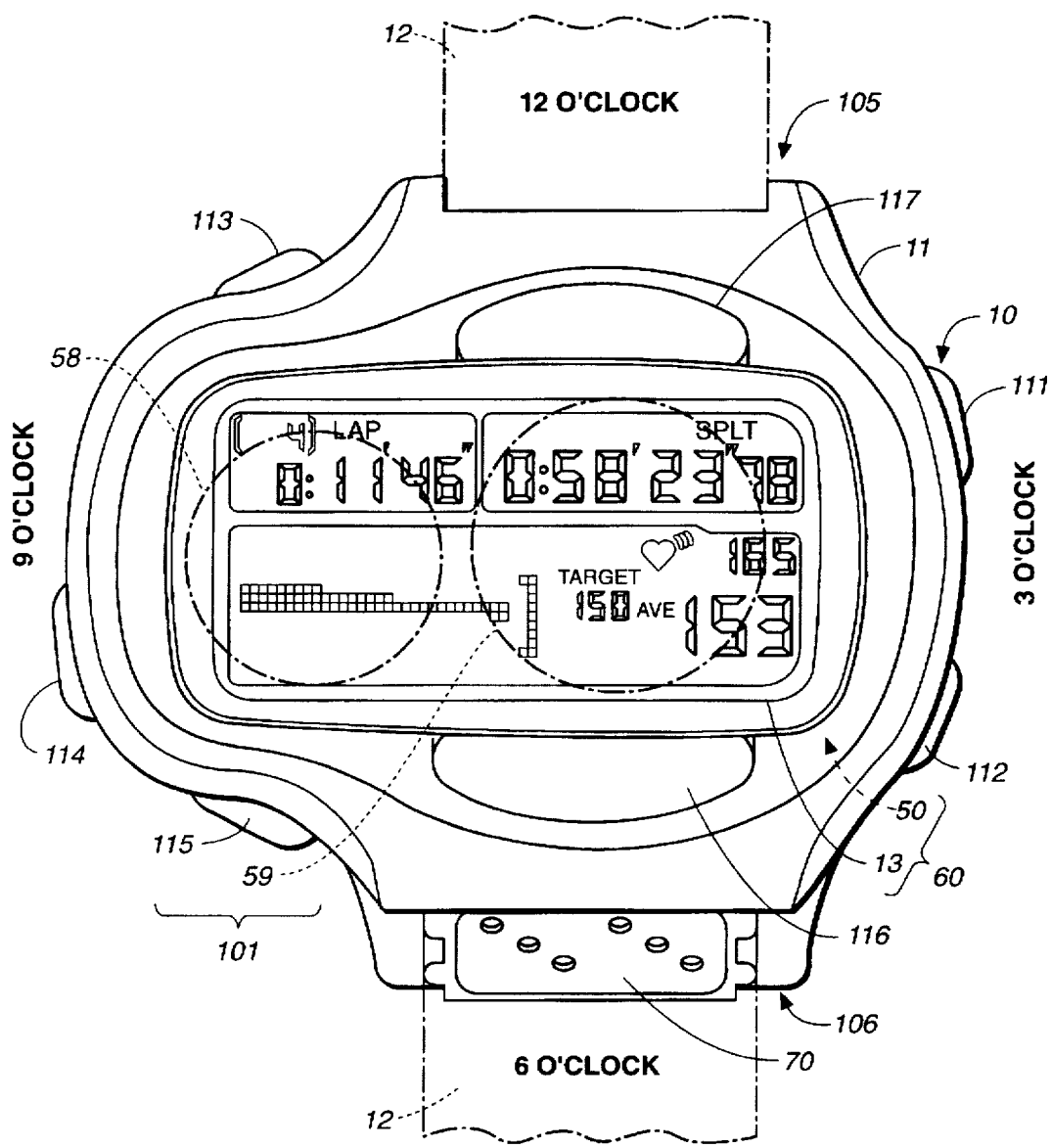
FIG._3

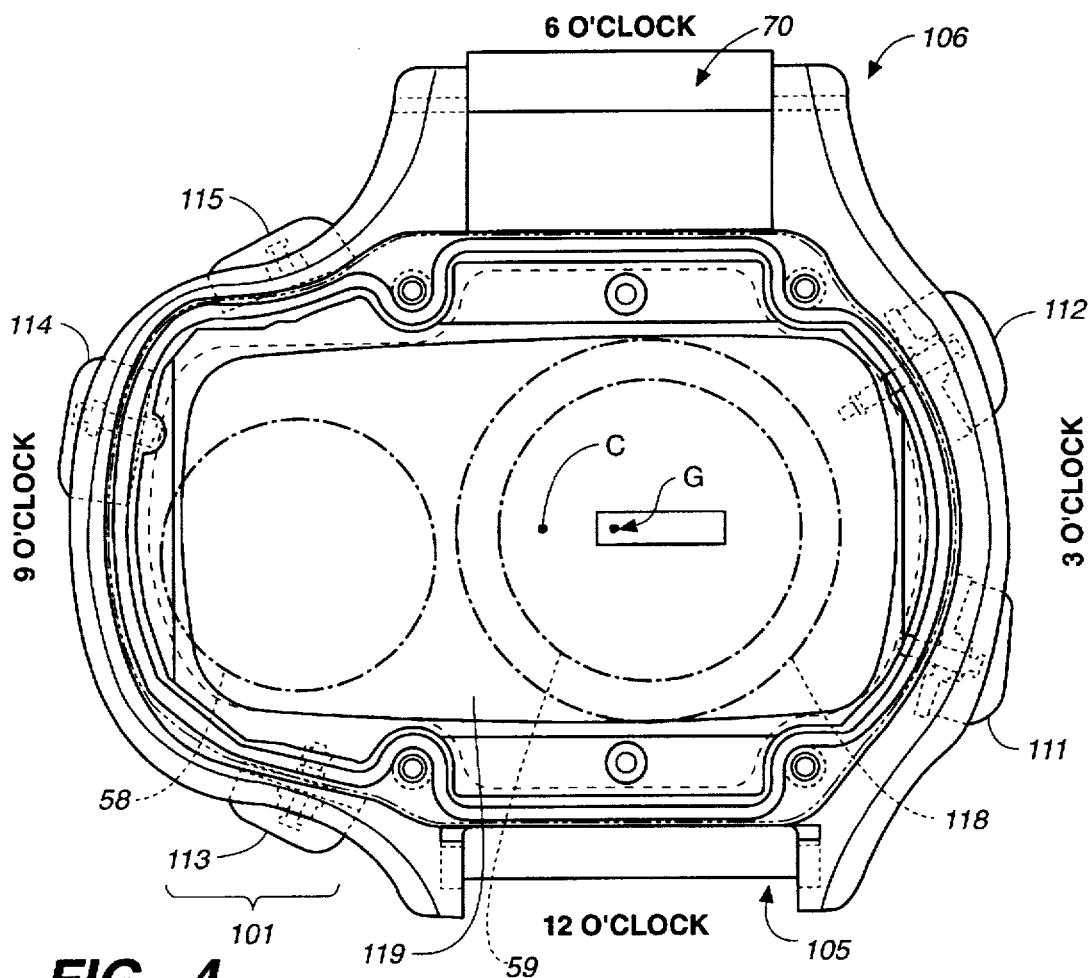
FIG._4
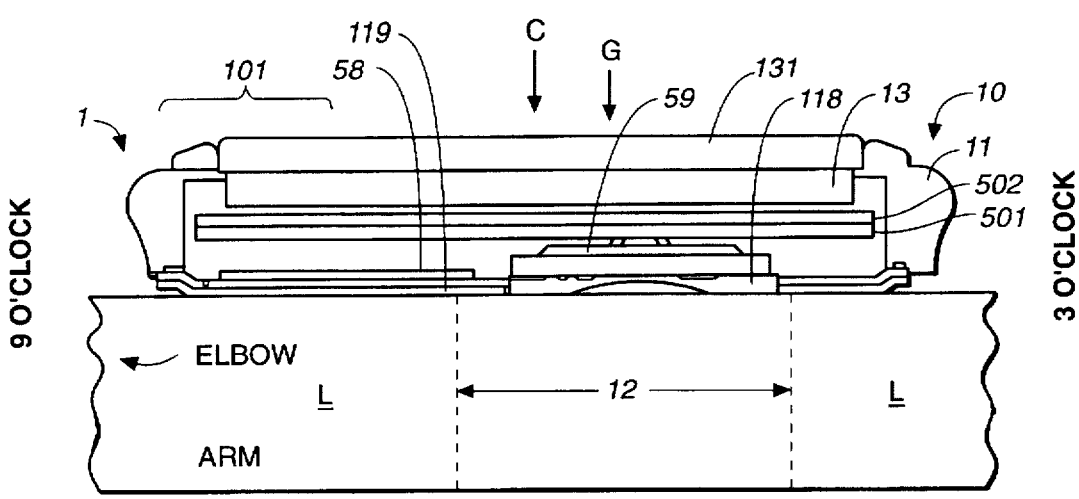
FIG._5

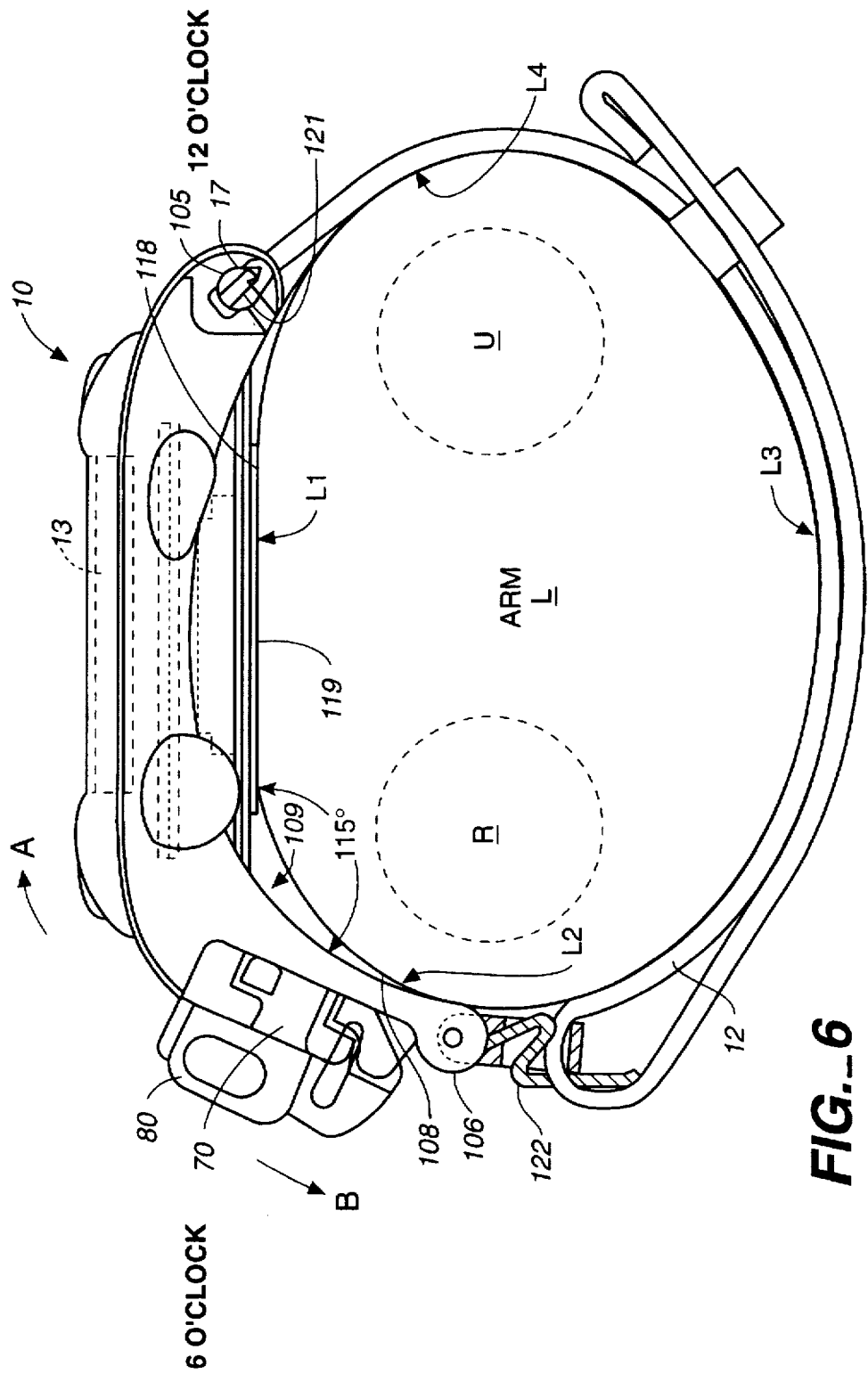
FIG._6

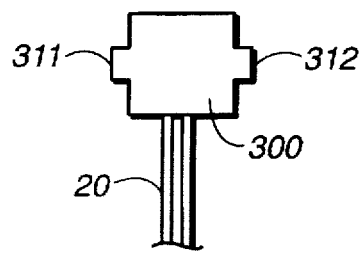
FIG._7A
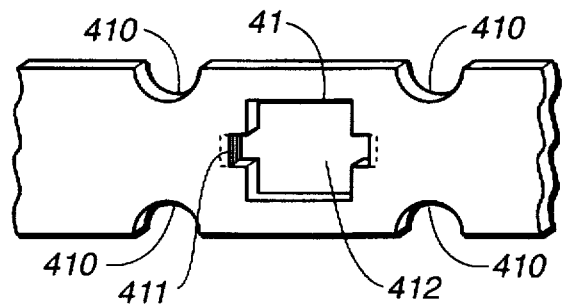
FIG._7B
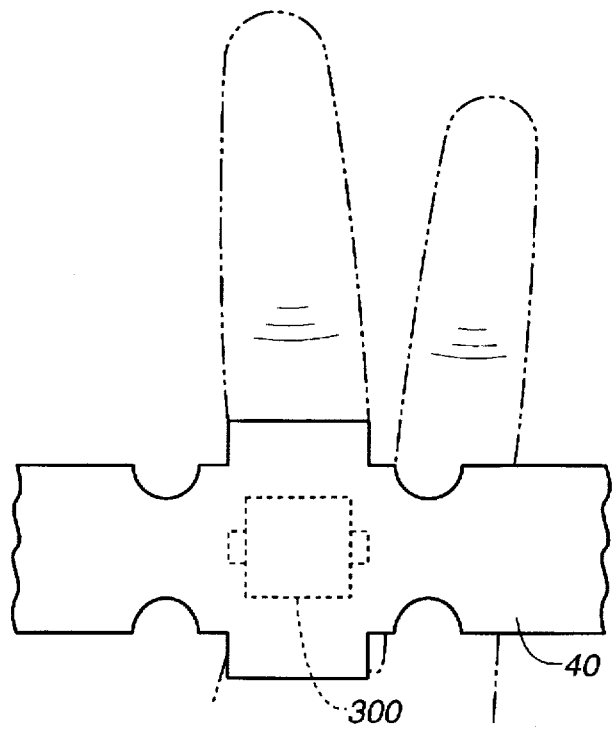
FIG._7C

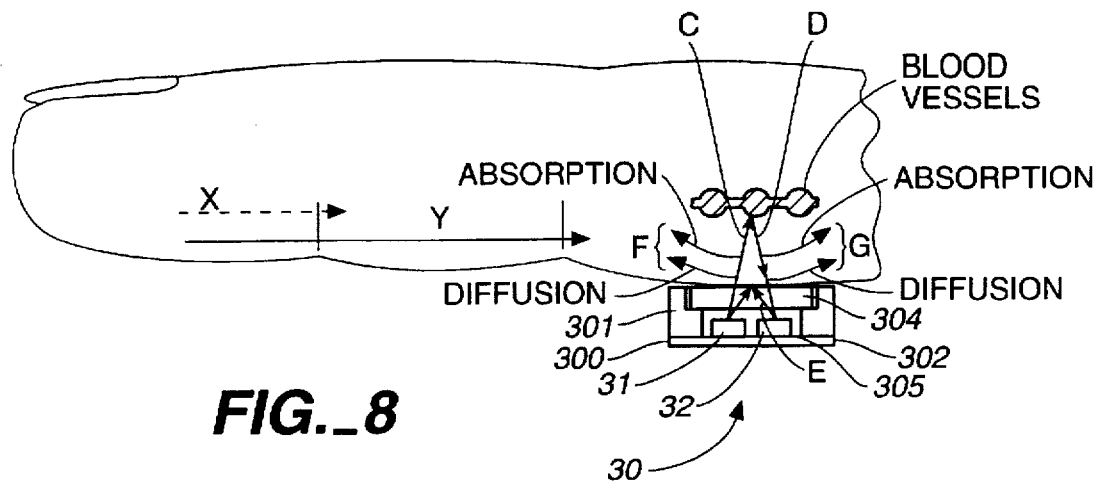
FIG._8
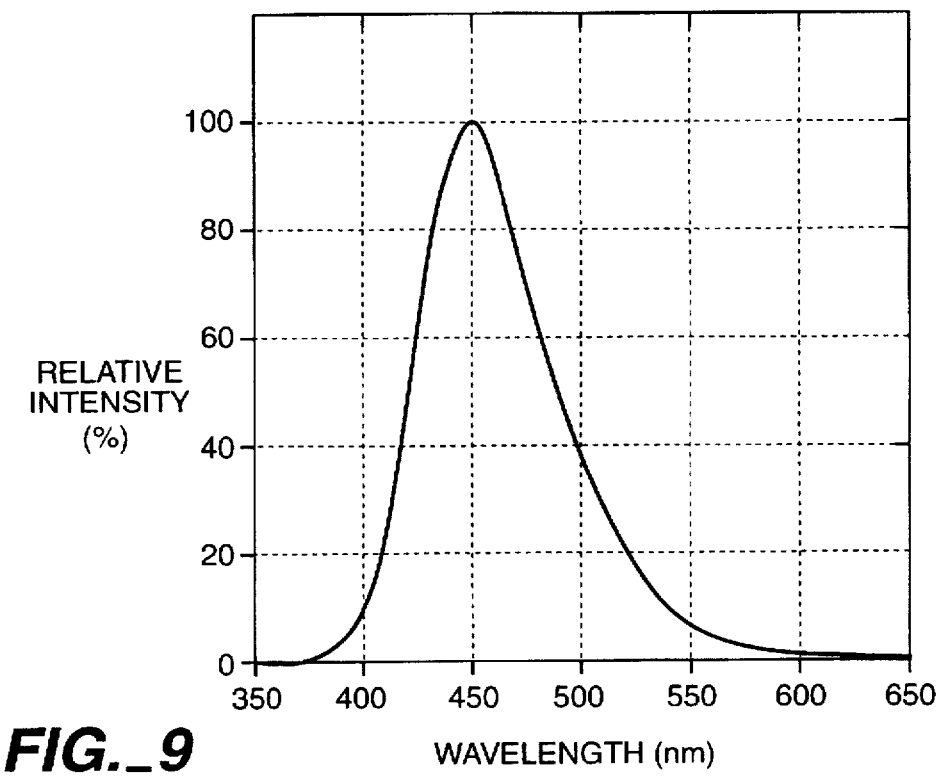
FIG._9

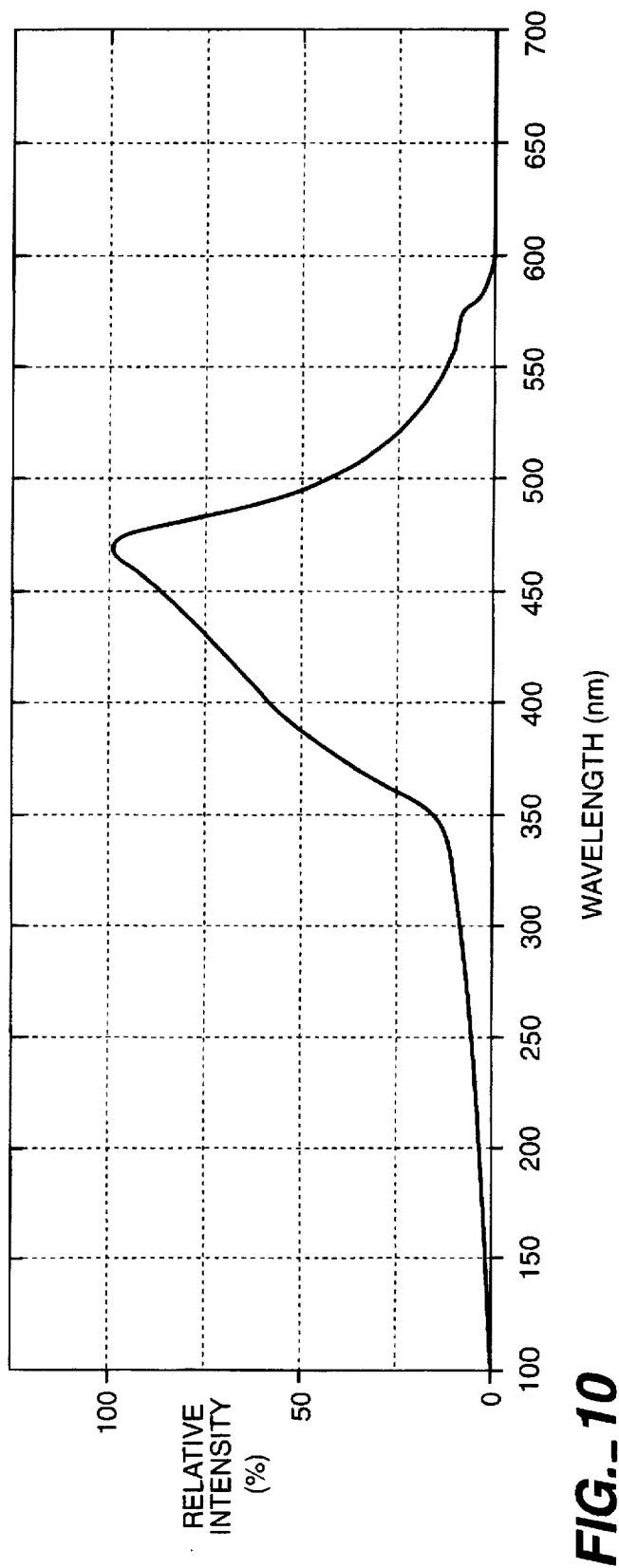
FIG._10

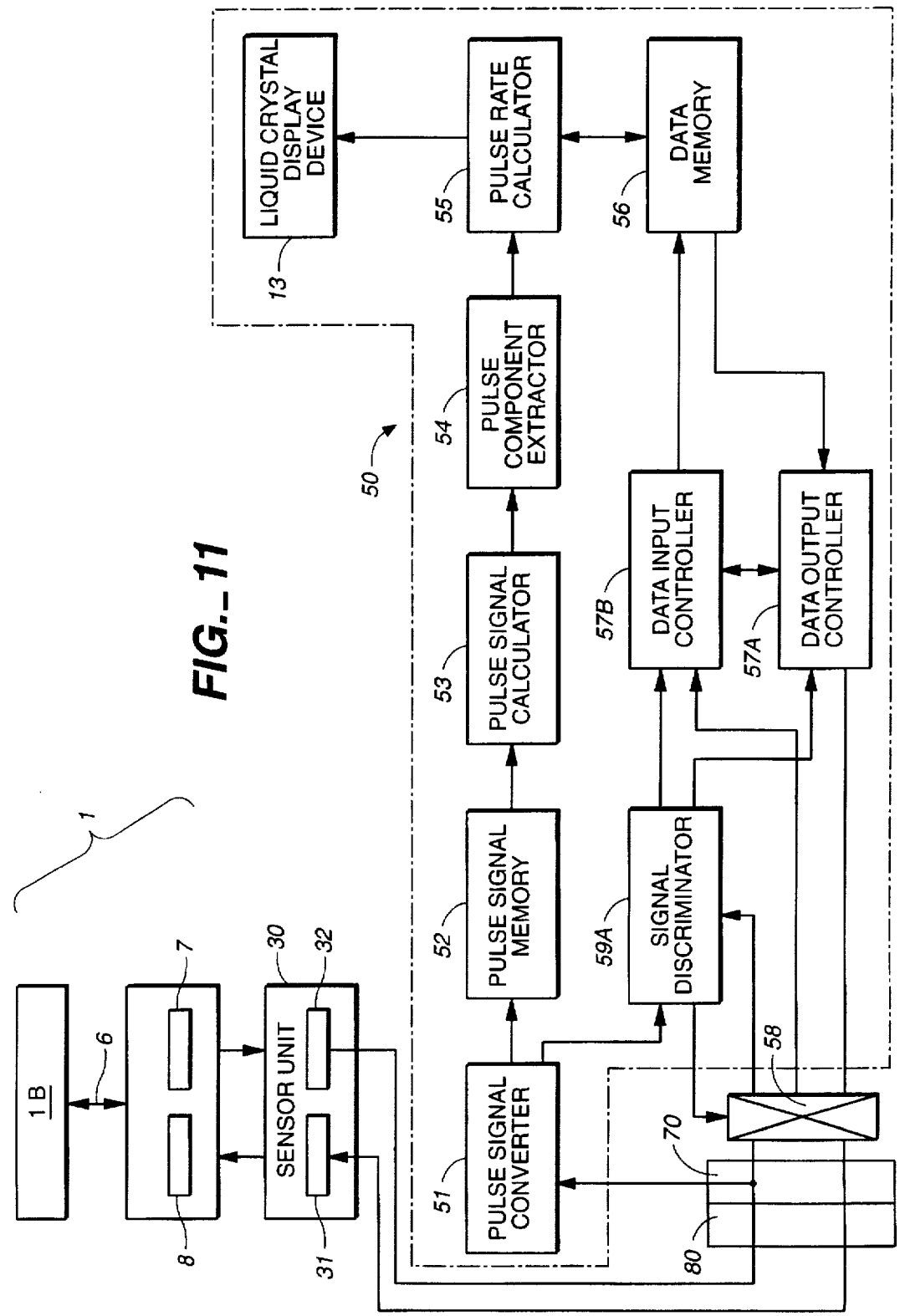

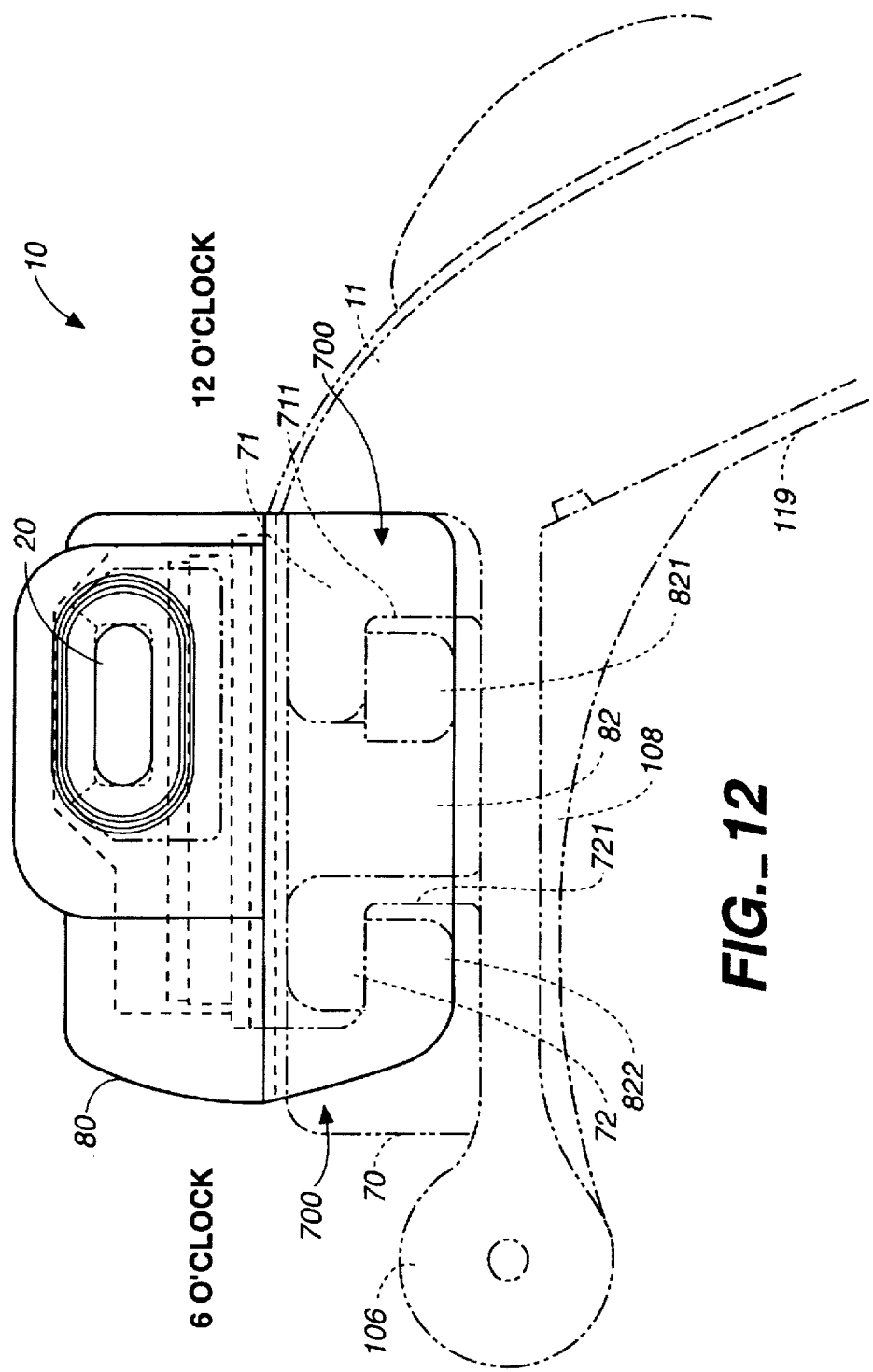
FIG._12

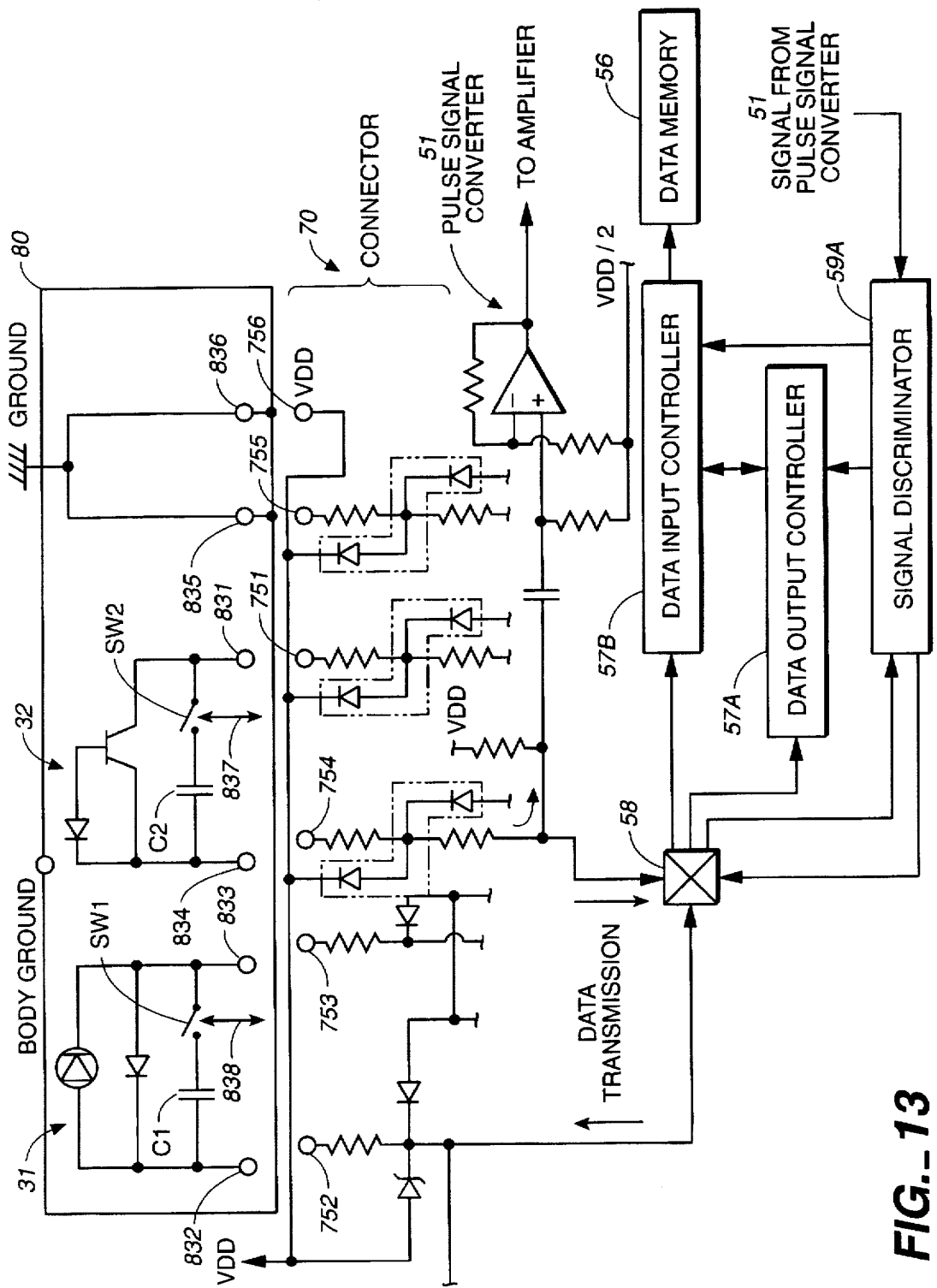
FIG._13

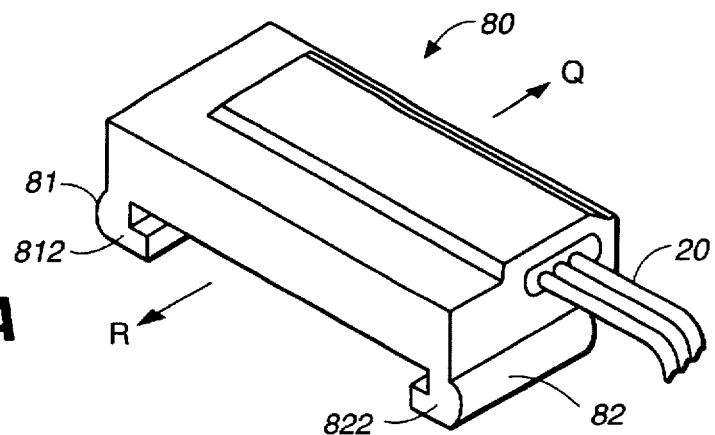
FIG._14A
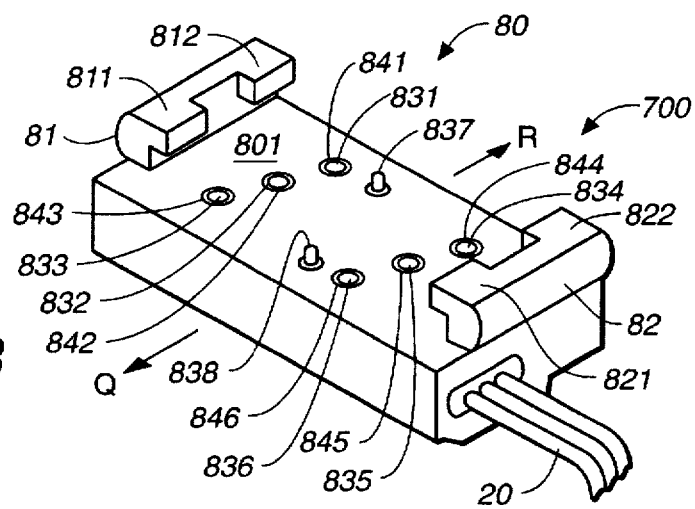
FIG._14B
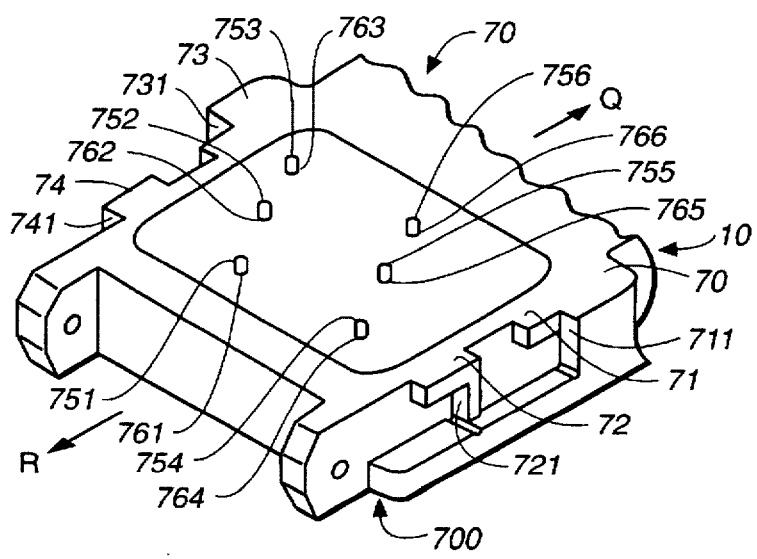
FIG._15

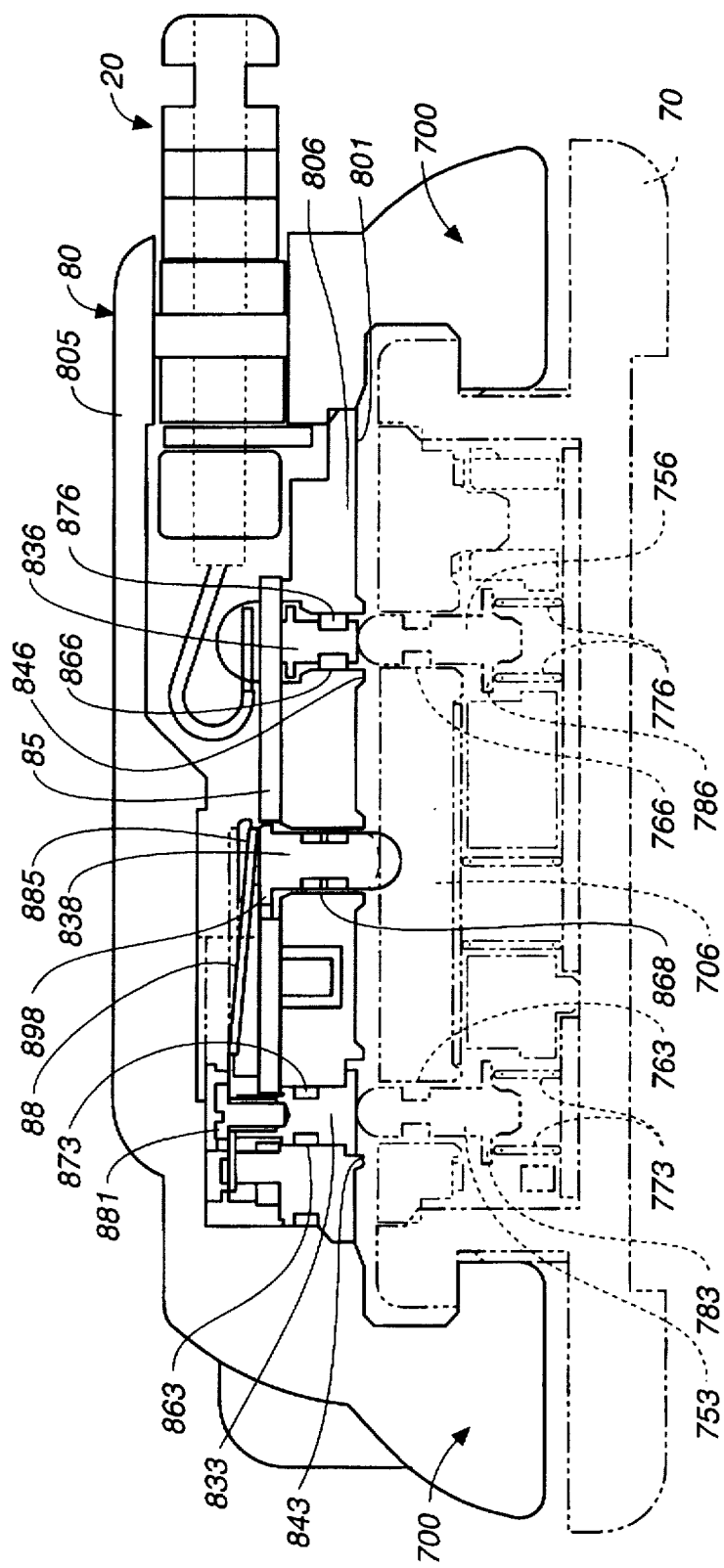
FIG._16

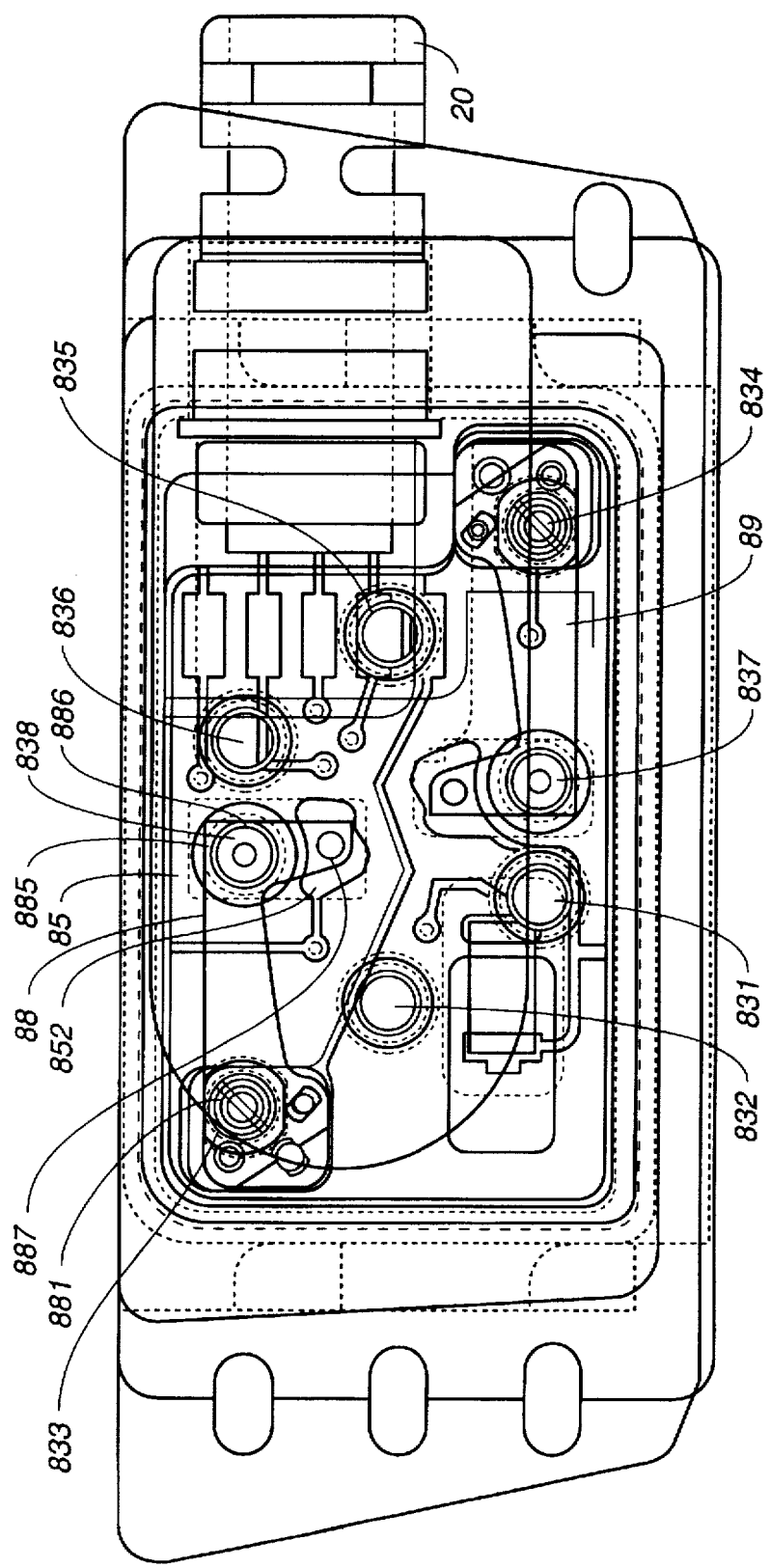
FIG._17

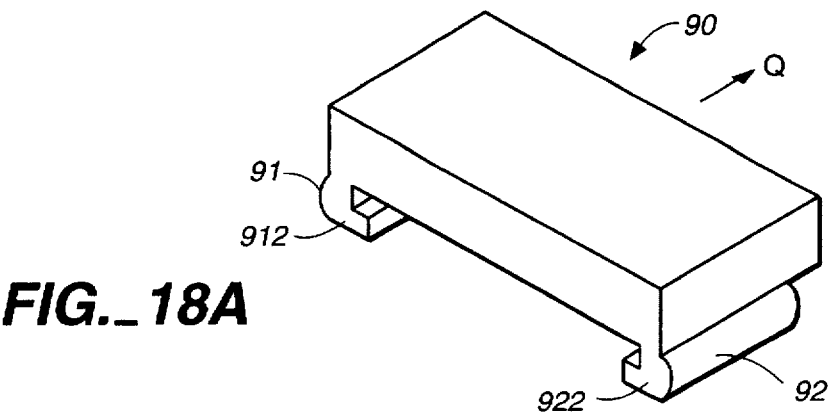
FIG._18A
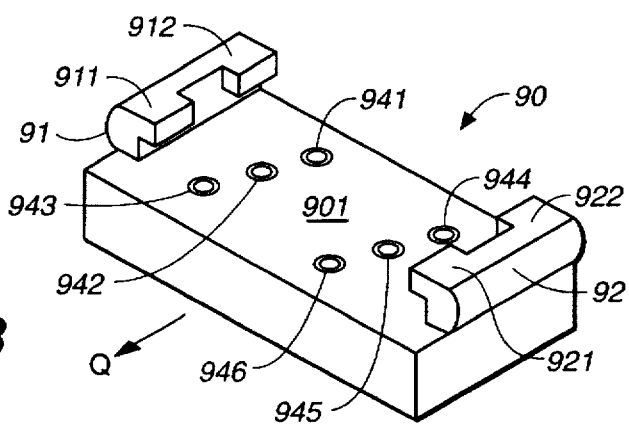
FIG._18B
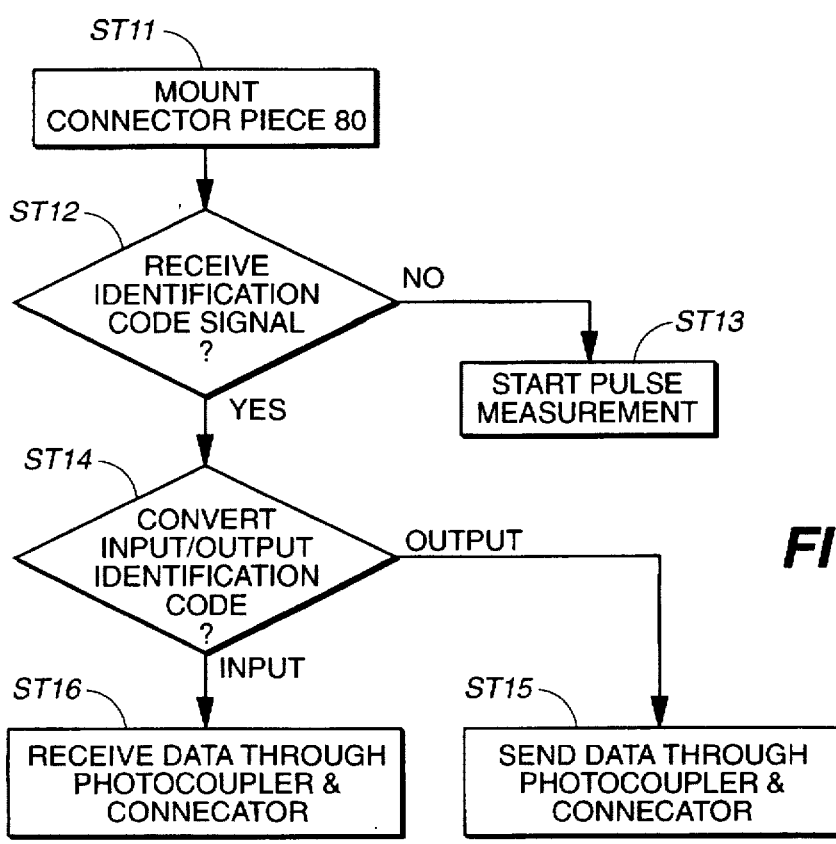
FIG._19

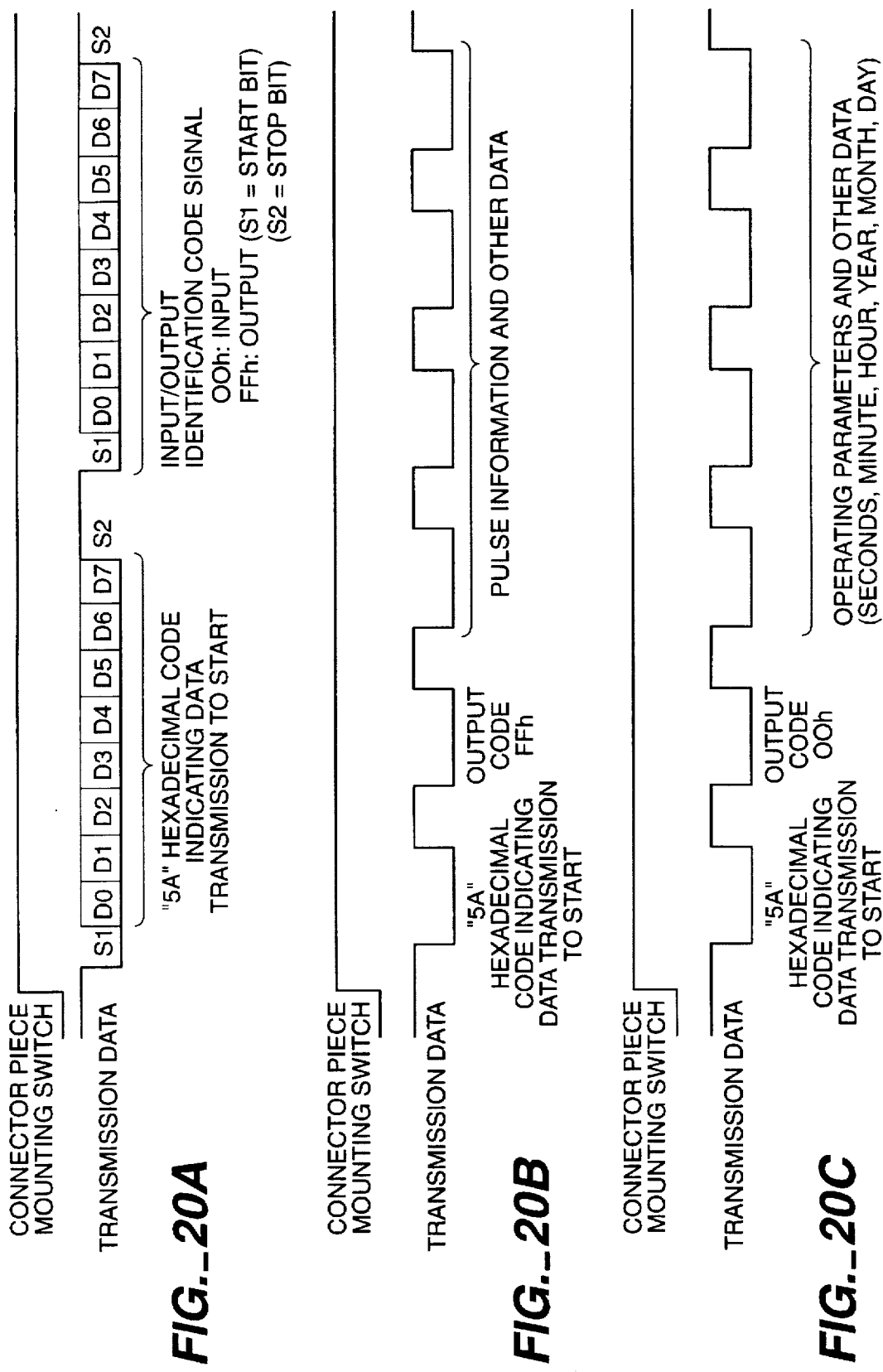

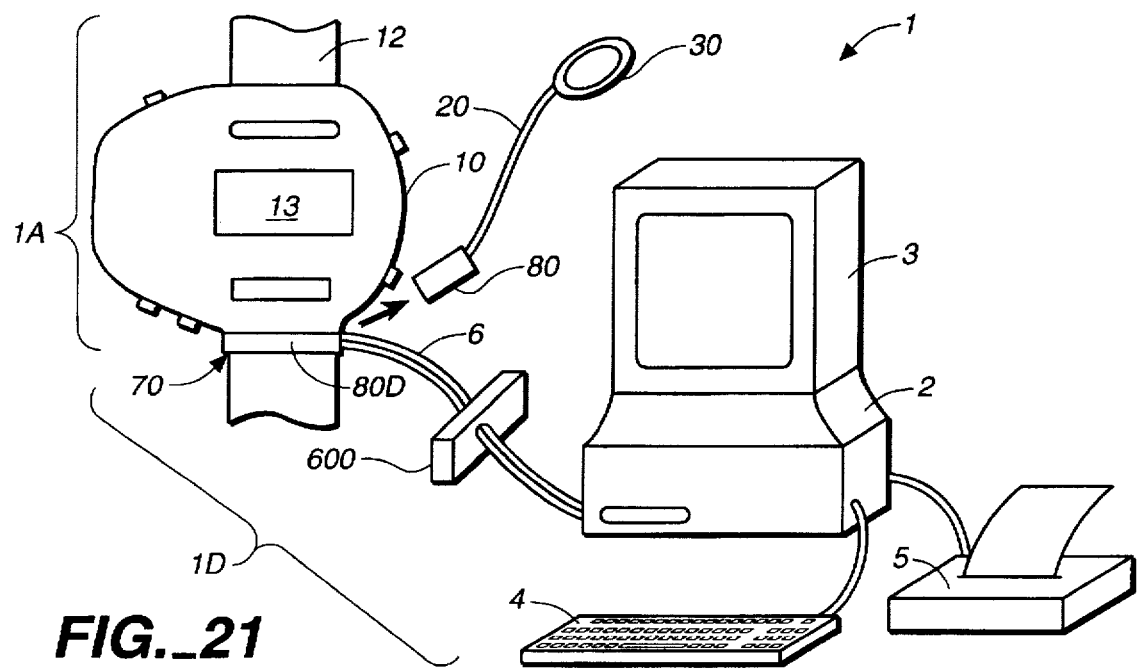
FIG._21
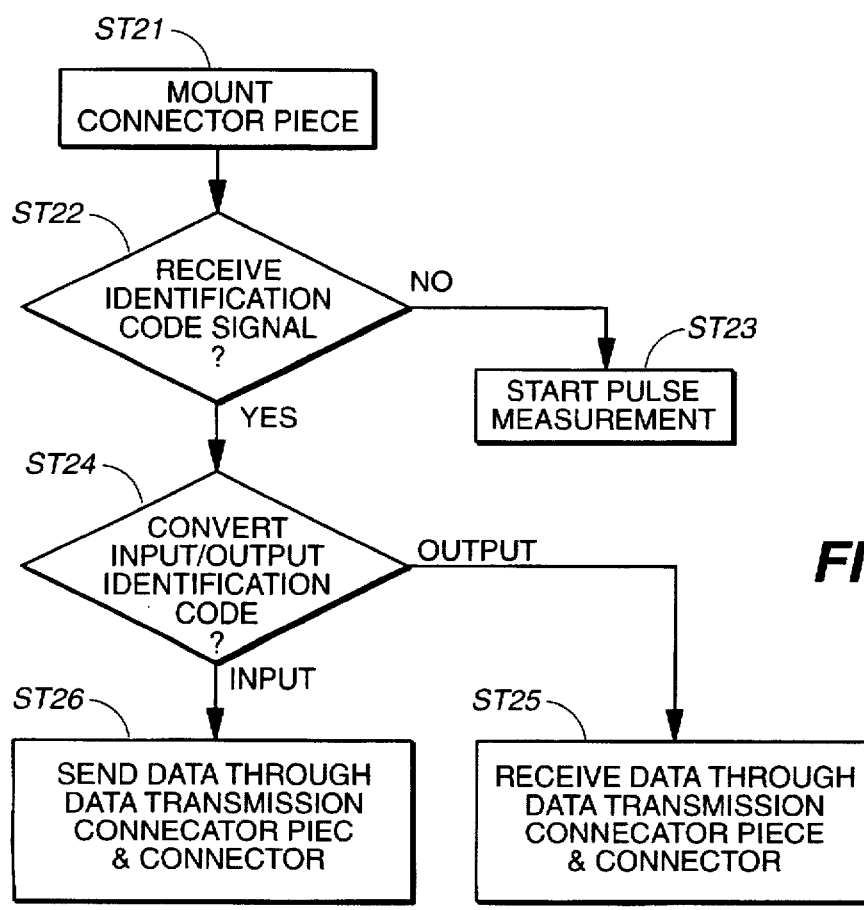
FIG._24

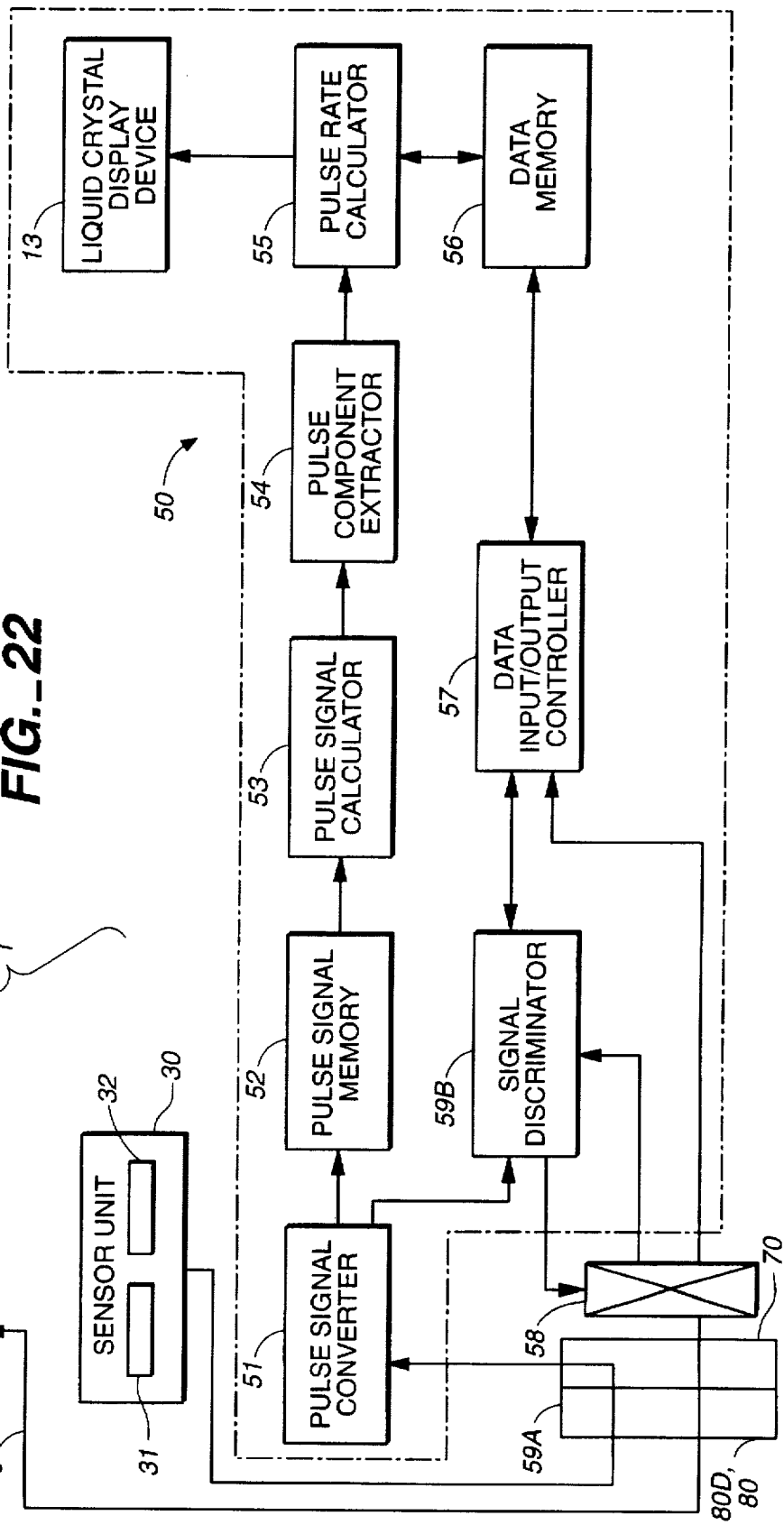
FIG._22

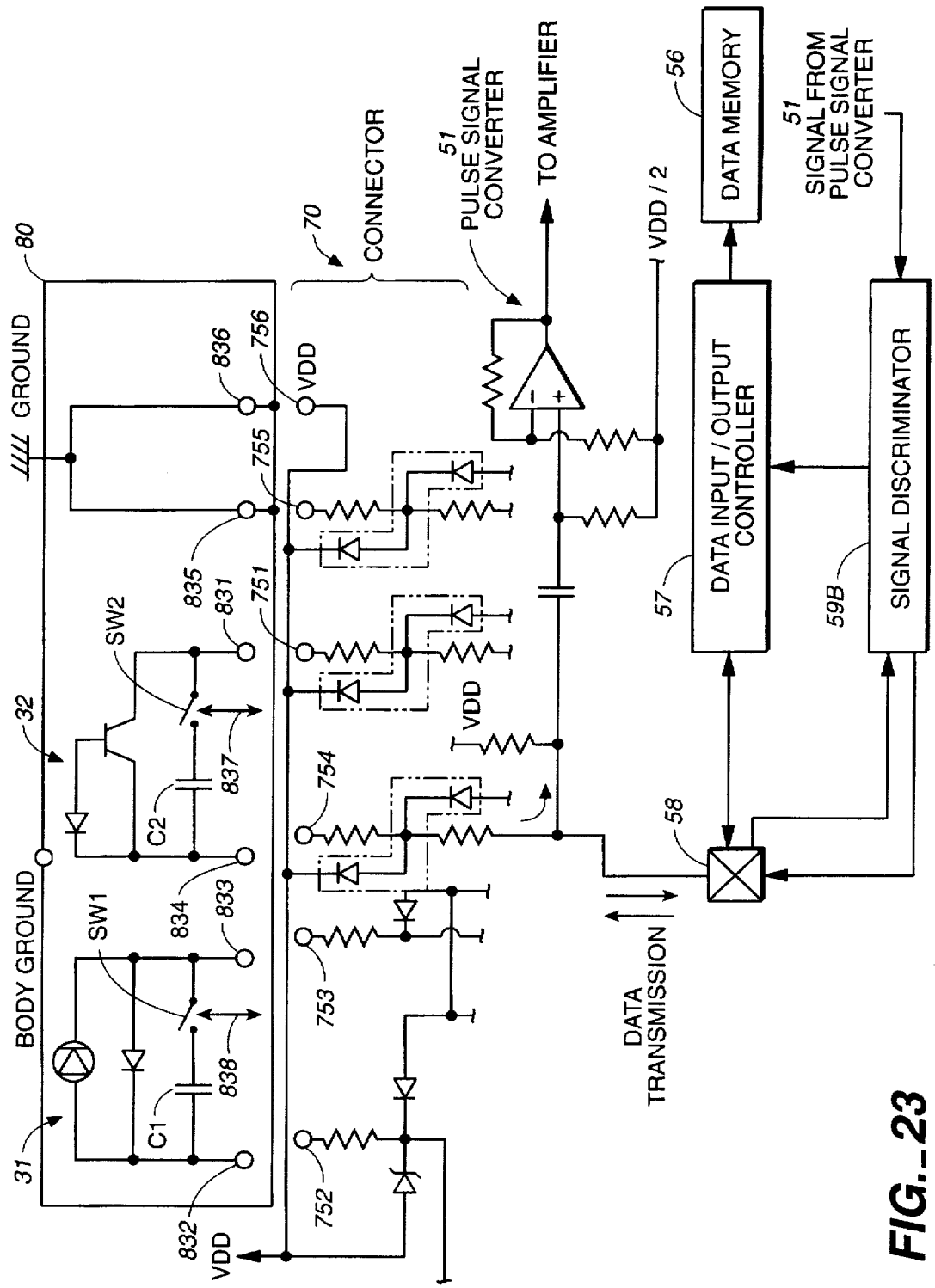
FIG._23

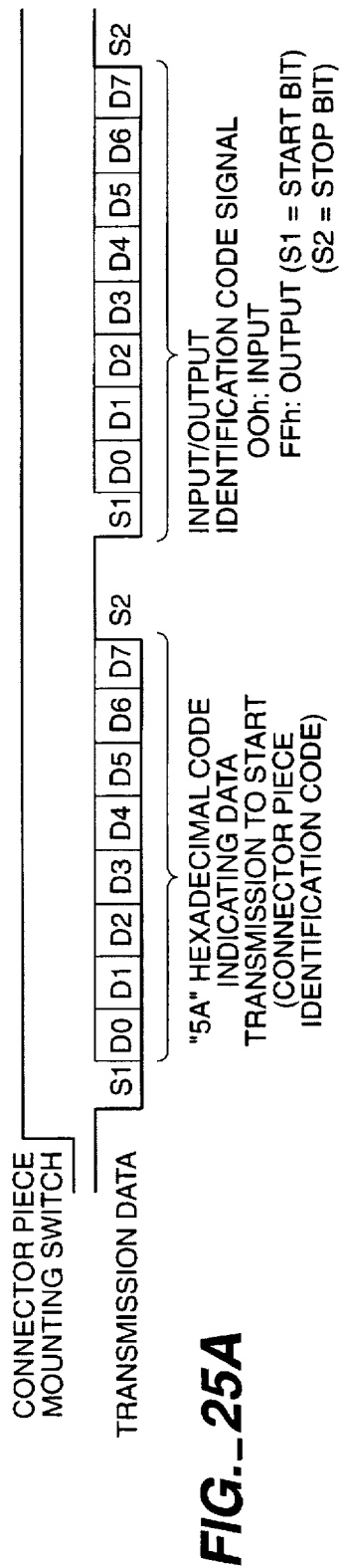
FIG._25A
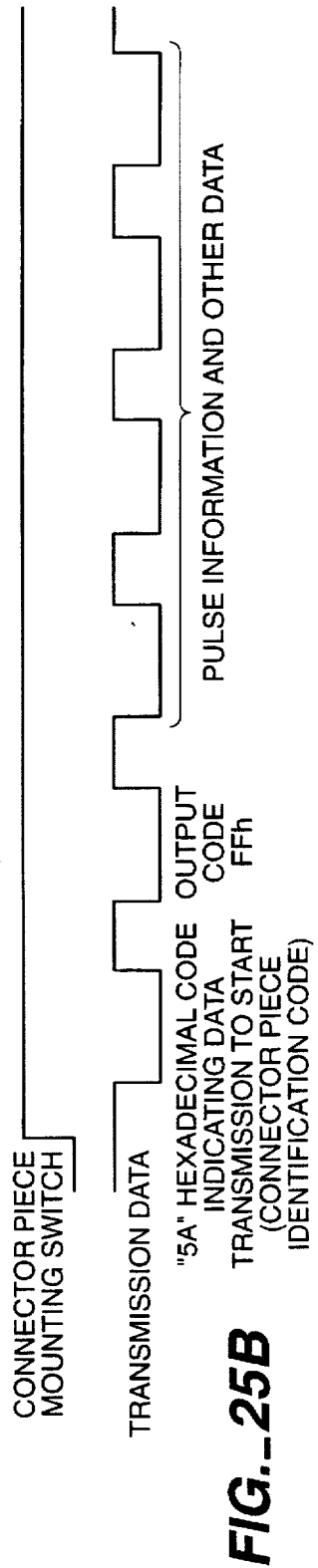
FIG._25B
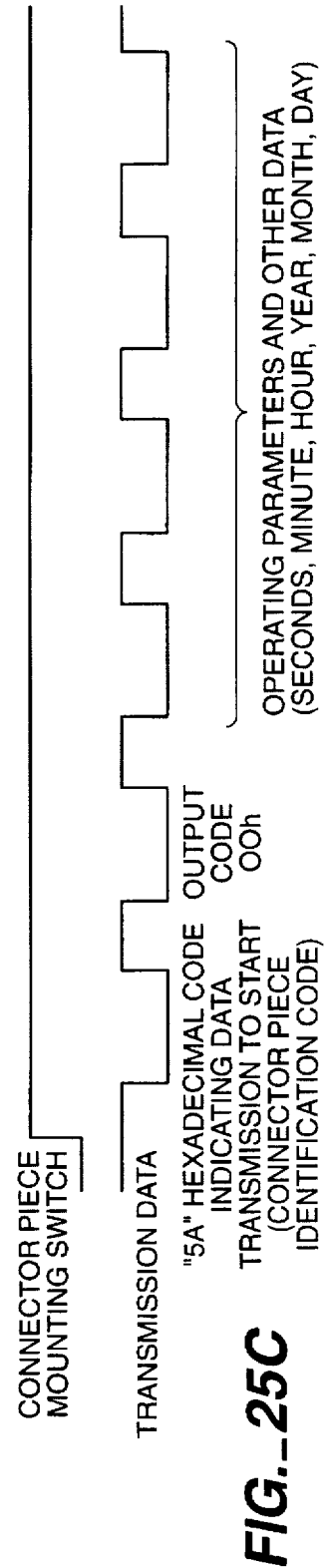
FIG._25C

WRIST-WORN PORTABLE DEVICE AND A WRIST-WORN PULSE WAVE MEASURING DEVICE

BACKGROUND OF THE INVENTION

1. Field of the Invention

This invention relates generally to a wrist-worn pulse wave measuring device for measuring such pulse information as the pulse rate of a user, and to a pulse information processing apparatus comprising the wrist-worn pulse wave measuring device. More specifically, the present invention relates to a technology for transmitting data between the wrist-worn pulse wave measuring device and a personal computer or other external device.

2. Description of the Related Art

One type of wrist-worn portable device capable of displaying various information optically detects changes in the blood level to display the pulse rate or other pulse information based on the detection results.

The sensor unit of this optical pulse wave measuring device comprises a light-emitting element, such as a light-emitting diode (LED), and an optical receptor, such as a phototransistor, and is typically worn on a finger. The light beam emitted from the LED is reflected from the skin and blood vessels and detected by the phototransistor. By thus detecting the difference between the emitted and reflected light quantity, the change in blood volume can be expressed by a pulse signal. This pulse signal can then be used to display the pulse count or other information.

The sensor unit also comprises a connector piece at the end of a cable extending from the optical sensor, and is thus able to input the pulse signal to the device body by connecting this connector piece to the device body connector.

A runner, for example, can use this type of pulse wave measuring device to measure the pulse while running or jogging. Because it is worn on the wrist, incorporating a clock and timer function also makes it possible for the runner to measure the lap time, split time, and other time parameters while running. The runner can thus display this information on the display unit of the device body after a race or run is completed to obtain reference data that can be used to determine the running pace in the future.

When the functionality of such a wrist-worn pulse wave measuring device is increased, however, the amount and types of information displayed on the integral display unit of the device body also increase, and data processing requirements increase. The amount of information that can be displayed at one time on the display unit, however, is obviously limited in this conventional wrist-worn pulse wave measuring device. When tabulating the data gathered while running, it is therefore necessary to sequentially display the data in small units, and this can be quite inconvenient. Configuration of this pulse wave measuring device as a wrist-worn device also imposes a practical physical limit to the size of the display unit, and makes it difficult to significantly increase functions integral to the wrist-worn pulse wave measuring device.

SUMMARY OF THE INVENTION

Therefore, it is an object of the present invention to overcome the aforementioned problems.

It is another object of the present invention to provide a wrist-worn pulse wave measuring device capable of transmitting measurement data to an external device to enable fast data processing and display without increasing the size of the device body, and to provide a pulse information processing apparatus using such wrist-worn pulse wave measuring device.

In accordance with a first aspect of the present invention, a wrist-worn pulse wave measuring device comprises a wrist band for holding the device body on the wrist. A sensor unit is worn facing the body surface and comprising a light emitter and a receptor for measuring the pulse. A connector is provided for connecting and disconnecting the sensor unit from the device body, and the pulse signal detected by the sensor unit is input to the device body. A signal discrimination means enables data transmission between the device body and an external device by discriminating whether the signal input to the device body through the connector is the pulse wave signal detected by the sensor unit, or is a signal output from an external device.

The wrist-worn pulse wave measuring device of the present invention can easily determine the present operating state, i.e., whether it is being used in the data collecting mode or the data transmission mode, by comprising a signal discrimination means for discriminating whether the signal input to the device body through the connector is the pulse wave signal detected by the sensor unit, or is a signal output from an external device. Because it is therefore possible with the wrist-worn pulse wave measuring device of the present invention to exchange data with an external device, the collected measurement data can be batch processed and displayed by the external device. It is therefore also possible to quickly process and display the collected data on the external device. This communication capability also makes it possible to set various parameters for wrist-worn pulse wave measuring device operations from the external device, and to thereby improve the ease of use of the wrist-worn pulse wave measuring device.

When a photocoupler using the light emitter and receptor is formed between an external device and the sensor unit mounted to the connector in a wrist-worn pulse wave measuring device according to the invention, data transfers between the device body and the external device can also be accomplished through the photocoupler and connector. This configuration using a photocoupler can thus be used to reduce the size and weight of the wrist-worn pulse wave measuring device because the light emitter and receptor of the pulse wave measurement sensor unit originally incorporated to measure the pulse waves can be used by the photocoupler to transmit optical signals between the wrist-worn pulse wave measuring device and external device using start-stop synchronization data transmissions.

Data transmissions between the device body and external device can also be accomplished through the external data transmission connector and the device body connector when the data transmission connector of an external device is connected to the connector in place of the sensor unit. This configuration can also be used to reduce the size and weight of the wrist-worn pulse wave measuring device because data can be transmitted with electrical signals between the wrist-worn pulse wave measuring device and external device using the connector piece originally provided to connect the sensor unit.

When the data transmission connector of an external device is connected to the device body connector to transfer data between the device body and external device, the invention is preferably comprised to transmit data through an interface unit capable of converting the signal voltage levels used by the device body and external device, or converting the communications methods when the device body and external device use different communications protocols. When thus comprised, a personal computer can be used as the external device even when the device body outputs a clock synchronization signal because the clock synchronization signal output from the device body is converted to a start-stop synchronization signal.

When thus comprised to transfer the pulse information obtained based on the pulse signal detection results between the device body and the external device, a storage means for storing at least the pulse information obtained according to the pulse signal detection result is also provided to the device body. As a result, it is also possible to form a pulse information processing apparatus using the wrist-worn pulse wave measuring device and external device.

As described above, the wrist-worn pulse wave measuring device according to the present invention can send and receive information with an external device because it comprises a signal discrimination means for determining whether the signal input to the device body through the connector is a signal from the sensor unit or is a signal output from the external device. This is convenient because it enables the measurement results collected by the wrist-worn pulse wave measuring device to be batch processed by the external device. In addition, because the operating parameters of various operations performed by the wrist-worn pulse wave measuring device can be batch set from the external device, the user-friendliness of the wrist-worn pulse wave measuring device is improved.

When a photocoupler formed with the sensor unit is used for data transmission in a wrist-worn pulse wave measuring device according to the present invention, the pulse measurement light emitter and receptor originally provided for measuring the pulse can be used as is, making this configuration suited to reducing the size and weight of the wrist-worn pulse wave measuring device.

Other objects and attainments together with a fuller understanding of the invention will become apparent and appreciated by referring to the following description and claims taken in conjunction with the accompanying drawings.

BRIEF DESCRIPTION OF THE DRAWINGS

In the drawings wherein like reference symbols refer to like parts.

FIG. 1 is an illustration of the overall configuration of a pulse information processing apparatus using a wrist-worn pulse wave measuring device according to the present invention;

FIG. 2A is a descriptive diagram showing a wrist-worn pulse wave measuring device according to a preferred embodiment of the present invention when in use;

FIG. 2B is a cross-sectional view of a sensor unit of the device in FIG. 2A;

FIG. 3 is a plan view of the device body of the wrist-worn pulse wave measuring device shown in FIG. 2A;

FIG. 4 is a bottom view of the device body of the wrist-worn pulse wave measuring device shown in FIG. 2A;

FIG. 5 is a side view of the device body of the wrist-worn pulse wave measuring device shown in FIG. 2A from the six o'clock direction of a wristwatch;

FIG. 6 is a side view showing of the device body of the wrist-worn pulse wave measuring device shown in FIG. 2A from the three o'clock direction of a wristwatch;

FIG. 7A is a plan view of the optical unit of the sensor unit used in the wrist-worn pulse wave measuring device shown in FIG. 2A; FIG. 7B is a plan view showing the sensor securing band of the sensor unit used in this wrist-worn pulse wave measuring device when opened; and FIG. 7C is a descriptive diagram showing the structure of a separate sensor unit;

FIG. 8 shows the wrist-worn pulse wave measuring device shown in FIG. 2A with the senor unit attached to the finger;

FIG. 9 is a graph showing the emissions spectrum of an InGaN blue LED used in the wrist-worn pulse wave measuring device shown in FIG. 2A;

FIG. 10 is a graph of the light reception characteristics of an InGaP phototransistor used in the wrist-worn pulse wave measuring device shown in FIG. 2A;

FIG. 11 is a block diagram showing the functions of the data processing circuit of the wrist-worn pulse wave measuring device shown in FIG. 2A;

FIG. 12 is an enlarged view of the connector of the wrist-worn pulse wave measuring device shown in FIG. 2A seen from the direction of three o'clock on a wristwatch;

FIG. 13 shows the electrical connections in the connector of the wrist-worn pulse wave measuring device shown in FIG. 2A;

FIGS. 14A and 14B show the structure of the connector piece used in the connecting means shown in FIG. 12;

FIG. 15 shows the structure of the connector used in the connector shown in FIG. 12;

FIG. 16 is a cross-sectional view showing the connector piece shown in FIGS. 14A and 14B mounted to the connector shown in FIG. 15;

FIG. 17 is a plan view showing the positions of the electrodes in the connector piece shown in FIGS. 14A and 14B;

FIGS. 18A and 18B show the structure of a connector cover covering the connector and substituted for the connector piece in the wrist-worn pulse wave measuring device shown in FIG. 2A;

FIG. 19 is a flow chart of the data transmission operation using the pulse information processing apparatus shown in FIG. 1;

FIGS. 20A–20C are waveform diagrams of the signals used for data transmission in the pulse information processing apparatus shown in FIG. 1;

FIG. 21 is an illustration of the overall configuration of a pulse information processing apparatus according to a second embodiment of the present invention;

FIG. 22 is a functional block diagram of the of the functions of the data processor of the wrist-worn pulse wave measuring device used in the pulse information processing apparatus shown in FIG. 21;

FIG. 23 is a diagram showing the circuit configuration of the connector of the wrist-worn pulse wave measuring device used in the pulse information processing apparatus shown in FIG. 21;

FIG. 24 is a flow chart of the data transmission operation using the pulse information processing apparatus shown in FIG. 21; and FIGS. 25A–25C are waveform diagrams of the signals used for data transmission in the pulse information processing apparatus shown in FIG. 21.

DESCRIPTION OF THE PREFERRED EMBODIMENTS

Overall configuration

FIG. 1 is an illustration of the overall configuration of a pulse information processing apparatus according to the present invention, and FIGS. 2A and 2B are descriptive illustrations showing the wrist-worn pulse wave measuring device that is part of the pulse information processing apparatus shown in FIG. 1 in use.

As shown in FIG. 1, pulse information processing apparatus 1 comprises wrist-worn pulse wave measuring device 1A and data processor 1B (or external device) for communicating data with wrist-worn pulse wave measuring device 1A.

The data processor 1B typically comprises central processing unit (CPU) 2, display 3, keyboard 4, and printer 5. The data processor 1B further comprises interface adapter 9 at the end of data transmission cable 6 leading from CPU 2.

Adapter 9 in turn comprises data transmission LED 7 (light emitting unit for data transmission) and data transmission photodiode 8 (data transmission receiver).

It should be noted that data processor 1B can be essentially any common personal computer, and detailed description of the internal configuration thereof is thus omitted below. It is also important to note, however, that a data transmission controller for sending and receiving data over data transmission cable 6 is built integrally with data processor 1B.

Referring to FIGS. 2A and 2B, wrist-worn pulse wave measuring device 1A (wrist-worn portable device) according to the present embodiment comprises device body 10 having a wristwatch construction, and sensor unit 30 with cable 20 for connecting to device body 10.

Wrist band 12 is disposed to device body 10 and is wrapped around the arm from the direction of twelve o'clock on the wristwatch and fastened to device body in the direction of six o'clock; this wrist band 12 enables device body 10 to be worn freely on the arm.

Note also that "in the direction of _o'clock" or "the position of _o'clock" in the present description refers to the orientation of the device body referenced to a typical analog wristwatch, and does not mean that the display on the device body is a dial-type (or analog) display.

Sensor unit 30 also comprises a sensor securing band 40 that is approximately 10 mm wide, and is held by sensor securing band 40 on the index finger between the knuckle and first joint.

Structure of the device body

FIG. 3 is a plan view of the device body of the wrist-worn pulse wave measuring device 1A according to the present embodiment; FIG. 4 is a bottom view of the device body; FIG. 5 is a descriptive diagram of the device body from the direction of six o'clock; and FIG. 6 is a descriptive diagram of the device body from the direction of three o'clock.

In FIG. 2A, a device body 10 comprises a resin watch case 11 (main case) with a liquid crystal display device 13 (display) on the top side of this watch case 11. Display device 13 is used to digitally display the pulse count and other pulse information in addition to the current time and date.

Data processor 50, which is used to process the detection signals to display the change in pulse count, for example, based on the detection result (pulse signal) returned by sensor unit 30, is built in to watch case 11. This data processor 50 and liquid crystal display device 13 together comprise information display means 60. A stopwatch circuit is also built in to data processor 50, enabling information display means 60 to display the normal time, lap time, split time, and other time information on liquid crystal display device 13.

Button switches 111–115 used to select the various operating modes, including setting the time, display mode, pulse measuring mode, stopwatch mode, and data transmission mode, are also provided on the outside of watch case 11. Button switches 116 and 117 are also provided on the surface of watch case 11. As shown by the dot-dash line in FIG. 3, the power supply for wrist-worn pulse wave measuring device 1A is button-type battery 590 housed inside watch case 11. Cable 20 supplies power from battery 590 to sensor unit 30, and inputs the detection results from sensor unit 30 to data processor 50 inside watch case 11.

As the functions of wrist-worn pulse wave measuring device 1A are increased, it is also necessary to enlarge device body 10, but because of the limitations imposed by device body 10 being worn on the arm, device body 10 cannot be enlarged in the directions of six o'clock and twelve o'clock. A horizontally long watch case 11 in which the length in the direction of three o'clock and nine o'clock is greater than the length in the direction of six o'clock and twelve o'clock is therefore used for device body 10 in the present embodiment as shown in FIG. 3.

As shown in FIG. 4 and FIG. 5, wrist band 12 is therefore connected to watch case 11 at a position offset toward the three o'clock position from the center position C in the direction of three o'clock and nine o'clock. As a result, device body 10 has a large protrusion 101 in the direction of nine o'clock when viewed from the wrist band 12, but does not have a similarly large protrusion in the three o'clock direction. As a result, the wrist can be bent with relative freedom and comfort even though the watch case 11 is long from side to side. The back of the hand will also not strike the watch case 11 when, for example, the user falls and the hand is bent back because there is no large projection in the direction of three o'clock. The wrist-worn pulse wave measuring device 1A is also stable on the wrist because the large protrusion 101 at nine o'clock position is held tight to the skin. It is therefore also not necessary to use an unnecessarily wide wrist band 12 even though the watch case 11 is wide from side to side.

Using the wide side-to-side construction of watch case 11, flat battery 590 used for the power supply and flat piezoelectric device 580 used for a buzzer are arrayed side by side in the planar direction (at roughly the three o'clock and nine o'clock positions) inside watch case 11, thus reducing the thickness of device body 10. With the battery 590 and piezoelectric device 580 arrayed side by side, it is also possible to provide battery cover 118 on back 119, and thus achieve a structure whereby the user can easily replace battery 590.

Battery 590, which is relatively heavy compared with the other electronic components, is also disposed offset from center position C near the three o'clock, while piezoelectric device 580, which is relatively light, is similarly disposed at a position offset toward nine o'clock. Thus, because battery 590 is heaver than piezoelectric device 580, the center of gravity G in the directions of three o'clock and nine o'clock on device body 10 is offset from the center position C in the direction of three o'clock. As a result, wrist band 12 is also attached closer to the three o'clock position and closer to the true center of gravity, and can thereby hold device body 10 stably on the arm.

As will also be known from FIG. 5, analog circuit board 501 and digital circuit board 502 comprising the data processor 50 are disposed one over the other on the display surface side of piezoelectric device 580 and battery 590, and liquid crystal display device 13 is disposed thereabove on the display surface side of data processor 50. Note also that cover glass 131 covers the outside surface side of liquid crystal display device 13.

Structure stopping the device body from rotating around the wrist

Referring to FIG. 6, a connecting member 105 for holding the holding pin 121 attached to the end of wrist band 12 is formed on the outside of watch case 11 at the twelve o'clock position. A holder 106 is formed on the outside of watch case 11 at the six o'clock position, and a fastener 122 is attached to holder 106. Wrist band 12 is wrapped around the wrist and folded back around fastener 122 at some intermediate lengthwise position, and held by fastener 122.

Turning stop 108 forming an approximately 115° angle to back 119 is formed integrally to watch case 11 extending from the edge of flat back 119 in which battery cover 118 is formed to holder 106 at the six o'clock position of device body 10.

As a result, when wrist-worn pulse wave measuring device 1A is secured to the wrist by wrist band 12 such that device body 10 is positioned at the top L1 (the same side as the back of the hand) of the left wrist L (arm), back 119 of watch case 11 is tight against top L1 of wrist L, and turning stop 108 is touching side L2 on the same side of the arm as the radius R. In this position, back 119 of device body 10 straddles the radius R and ulna U of the arm through the skin, and curved part 109 between turning stop 108 and back 119 which is pressed against the radius R of the arm through the skin.

Because turning stop 108 and back 119 form an anatomically ideal angle of approximately 115°, attempts to turn device body 10 from the position in FIG. 6 in the direction of arrow A, i.e., to turn device body 10 around wrist L from the front to the other side, are stopped by turning stop 108 in contact with side L2 of the wrist L, and device body 10 does not shift. Conversely, attempts to turn device body 10 in the direction of arrow B, i.e., attempts to turn device body 10 around the wrist L toward the front, are stopped by back 119 of device body 10 in contact with the top L1 of the wrist L, and device body 10 does not shift.

The user can therefore read the display device 13 by simply bending the elbow slightly with the wrist-worn pulse wave measuring device 1A worn on the wrist because the weight of the device body 10 will not cause the wrist-worn pulse wave measuring device 1A to turn unnecessarily around to the far side of the wrist L. The narrow view angle of the liquid crystal display device 13 makes it difficult, and thus inconvenient, to read the content displayed on the liquid crystal display device 13 when the position of the device body 10 shifts slightly, but this problem is avoided with the wrist-worn pulse wave measuring device 1A according to the present invention.

Furthermore, because device body 10 does not completely contact the entire circumference of the wrist L and there is a partial gap to the surface of the wrist L, wearing comfort is not impaired by providing turning stop 108. Note that rotation around the wrist is prevented at only two places on one side by back 119 and turning stop 108. As a result, rotation is effectively prevented even when the arm is thin because back 119 and turning stop 108 reliably contact the arm, and there is no constricted feeling when the arm is thick.

It should also be noted that it has been confirmed that rotation of device body 10 around the arm can be reliably prevented if the angle formed by back 119 and turning stop 108 is between approximately 105° to approximately 125°. It should also be noted that wrist-worn pulse wave measuring device 1A may be worn with device body 10 positioned at the bottom L3 (the same side as the palm) of the wrist L, in which case turning stop 108 of device body 10 is positioned in contact with side L4 on the same side as the ulna U. Even in this position, device body 10 will not rotate unnecessarily whether force is applied in the direction of arrow A or arrow B.

Sensor unit configuration

FIG. 7A is a plan view of the optical sensor unit of the sensor unit used in the wrist-worn pulse wave measuring device according to the present embodiment; FIG. 7B is a plan view showing the band for securing the sensor of the sensor unit used in this wrist-worn pulse wave measuring device when the band is laid flat; FIG. 7C shows the structure of an alternative sensor unit; and FIG. 8 is a diagram showing the sensor unit when worn at the base of the finger.

Referring again to FIG. 2A, sensor unit 30 comprises sensor securing band 40 and optical sensor unit 300. Connector piece 80 is provided on the end of cable 20 extending from optical sensor unit 300, and can be freely connected to and disconnected from connector 70 of device body 10. As a result, when connector piece 80 is connected to connector 70 of device body 10, sensor unit 30 can input signals to device body 10 through connector 70.

Sensor securing band 40 is made from a flexible, thick resin molding which is spread open from a normally circular configuration, fit over the base of the finger, and then released, allowing the inherent shape retention of the band to wrap the band around the base of the finger. The middle part of sensor securing band 40 is thicker, and a hole 41 for holding optical sensor unit 300 is formed therein.

Referring to FIG. 7A, optical sensor unit 300 is enclosed in a rectangular resin molding comprising a pair of flanges 311 and 312 on the side with cable 20 leading from the inside of this optical sensor unit 300.

In FIG. 7B, hole 41 in sensor securing band 40 is a shape and size allowing optical sensor unit 300 to be embedded therein, and comprises recesses 411 and 412, in which flanges 311 and 312 are fit when optical sensor unit 300 is fit in hole 41, to prevent optical sensor unit 300 from falling out.

Note also that constricted parts 410 are formed in four places in sensor securing band 40 to enable easier fitting to the finger.

Because it is sufficient to be able to lightly clench the hand when the sensor unit 30 is worn at the base of the finger, there is no problem if the width of sensor securing band 40 is approximately 20 mm. A configuration in which the width of sensor securing band 40 is slightly wider in the part where optical sensor unit 300 is held can also be used as shown in FIG. 7C.

Optical sensor unit 300 and the sensor securing band of sensor unit 30 may also be completely separate members. For example, an elastic supporter type of band using an elastic, opaque expanded urethane rubber may be used for the sensor securing band. In this case, optical sensor unit 300 is inserted on the inside of the supporter-like band worn on the finger.

Referring to FIG. 8, optical sensor unit 300 comprises a sensor frame 301 as the case closed by bottom cover 302, thus forming a parts housing on the inside. Glass plate 304 (filter) forms a transparent window in the top of sensor frame 301, and circuit board 305 is secured inside sensor frame 301 opposing this glass plate 304. Pulse measurement LED 31, pulse measurement phototransistor 32, transistors (not shown), and other electronic components are mounted on circuit board 305 with pulse measurement LED 31 and pulse measurement phototransistor 32 oriented with the light emitting face and receptor face, respectively, facing glass plate 304.

As further described below, pulse measurement LED 31 and pulse measurement phototransistor 32 are used for optical signal data transmissions between wrist-worn pulse wave measuring device 1A and data processor 1B.

Specifically, recess 991 in which optical sensor unit 300 of sensor unit 30 is fit is formed in the top of adapter 9 shown in FIG. 1, and data transmission LED 7 and data transmission photodiode 8 are disposed at the bottom of recess 991. Thus, when optical sensor unit 300 is fit inside recess 991, pulse measurement LED 31 is in opposition to data transmission photodiode 8, and thus forms a photocoupler. Pulse measurement phototransistor 32 is similarly in opposition to data transmission LED 7, and forms a photocoupler.

In this embodiment an InGaN (indium-gallium-nitrogen) blue LED is used for pulse measurement LED 31. The emissions spectrum of this LED has an emissions peak at 450 nm as shown in FIG. 9, and an emissions wavelength range from 350 nm to 600 nm. Corresponding to the emissions characteristics of pulse measurement LED 31, a GaAsP (gallium-arsenic-phosphorus) phototransistor is used as pulse measurement phototransistor 32 in this embodiment. The detection range of this element has a primary sensitivity range from 300 nm to 600 nm with sensitivity also extending below 300 nm as shown in FIG. 10.

It is also possible to use a sensor unit adding a filter to this element as pulse measurement phototransistor 32. Because the power consumption of pulse measurement LED 31 and pulse measurement phototransistor 32 is relatively low, the continuous operating time is long even when both the clock functions and pulse wave measuring function are driven with a single compact battery as in wrist-worn pulse wave measuring device 1A according to the present embodiment.

Data processing circuit configuration

If sensor securing band 40 is worn at the base of the finger, the light emitting surface and receptor surface of pulse measurement LED 31 and pulse measurement phototransistor 32, respectively, also face the surface of the skin because optical sensor unit 300 is disposed to sensor securing band 40 such that glass plate 304 faces the inside as shown in FIG. 8. Therefore, when light is emitted from pulse measurement LED 31 toward the finger, the light reflected from the body (blood vessels) is detected by pulse measurement phototransistor 32, and optical sensor unit 300 inputs the detection result (pulse signal) to device body 10 via cable 20, connector piece 80, and connector 70, the pulse count can be obtained from the pulse signal by device body 10.

Referring to FIG. 11, a block diagram of part of the functions of the data processing circuit in the watch case, the pulse signal converter 51 of data processor 50 converts the signal input from sensor unit 30 by cable 20 to a digital signal, and outputs to pulse signal memory 52. Pulse signal memory 52 is RAM storing the pulse data converted to digital signals. Pulse signal calculator 53 reads and frequency analyzes the signal stored to pulse signal memory 52, and inputs the result to pulse component extractor 54. Pulse component extractor 54 extracts the pulse component from the input signal from pulse signal calculator 53, and outputs to pulse rate calculator 55. This pulse rate calculator 55 calculates the pulse count based on the input pulse wave frequency component, and outputs the result to liquid crystal display device 13.

Data processor 50 also comprises data memory 56 for storing the pulse count and other pulse information obtained by pulse rate calculator 55, time data corresponding to this pulse information, and the lap time, split time, and other time data measured using the stopwatch feature of the wrist-worn pulse wave measuring device 1A while running.

Data processor 50 further comprises data output controller 57A and data input controller 57B. Data output controller 57A outputs the pulse information and time information stored to data memory 56 from pulse measurement LED 31 of sensor unit 30 to data transmission photodiode 8 as an optical signal when wrist-worn pulse wave measuring device 1A is in the data transmission mode, and data input controller 57B stores the optical signal received from data transmission LED 7 through pulse measurement phototransistor 32 to data memory 56.

Data processor 50 further comprises signal discriminator 59A for identifying the signal input from sensor unit 30 through connector 70. When the input signal from sensor unit 30 is a common pulse signal, signal discriminator 59A holds analog switch 58 open to enable pulse wave measurement. When signal discriminator 59A determines that the signal input from sensor unit 30 is a signal from data processor 1B requesting the start of data transmission, signal discriminator 59A closes the open analog switch 58 to enable data transmission between wrist-worn pulse wave measuring device 1A and data processor 1B.

Connector means configuration

FIG. 12 is an enlarged view from the three o'clock position with the connector piece fit to the connector member. FIG. 13 illustrates the combination of sensor circuit electrodes on the connector piece side, and the connector member terminals for communicating signals with the sensor circuit.

So that wrist-worn pulse wave measuring device 1A according to the present embodiment can be used as a common wristwatch during normal everyday life, cable 20 and sensor unit 30 can be connected and disconnected at the side of device body 10 positioned near six o'clock as shown in FIG. 1. More specifically, a connector 70 is formed on the outside surface of the part extended as turning stop 108 at the six o'clock position on the edge of device body 10 such that connector piece 80 (connector member for pulse signal input) disposed on the end of cable 20 can be fit thereto as shown in FIG. 12.

Wrist-worn pulse wave measuring device 1A can therefore be used as a common wristwatch if sensor unit 30 and cable 20 are disconnected from device body 10.

Furthermore, because connector 70 is formed on the surface of the part corresponding to turning stop 108, the part extended to provide turning stop 108 can be used as is for connector 70. Connector 70 is also on the front when seen by the user with device body 10 worn on the arm because connector 70 is positioned near the six o'clock position, and operation is therefore simple. The user can also freely bend the wrist while running, and the back of the hand will not strike connector 70 even if the user falls while running, because connector 70 does not project at the three o'clock position from device body 10.

The electrical connections completed between connector 70 and connector piece 80 (connector means) are as shown in FIG. 13.

Referring to FIG. 13, terminals 751–756 (first terminal group) are disposed to connector 70, which is provided on the device body 10 side, and electrodes 831–836 (second terminal group) corresponding to these terminals 751–756 are disposed to connector piece 80. Terminal 752 is a positive terminal for supplying second drive voltage VDD to pulse measurement LED 31 through electrode 832; terminal 753 is a terminal set to the negative potential of pulse measurement LED 31 through electrode 833; terminal 754 is for supplying the constant drive voltage VREG to the collector terminal of pulse measurement phototransistor 32 through electrode 834; terminal 751 is the terminal to which the signal from the emitter terminal of pulse measurement phototransistor 32 is input through electrode 831; and terminal 755 is the terminal to which is input through electrode 835 the signal for detecting whether connector piece 80 is connected to connector 70. Electrode 836 grounds sensor unit 30 to the body, and shields electrodes 831–836 by making VDD the ground when terminal 756 and electrode 836 are electrically connected.

A first capacitor C1 and first switch SW1 are inserted between the pulse measurement LED 31 terminals (between electrodes 832 and 833) in connector piece 80. This switch SW1 is closed when connector piece 80 is disconnected from connector 70, connecting first capacitor C1 parallel to pulse measurement LED 31, and is open when connector piece 80 is connected to connector 70. A second capacitor C2 and second switch SW2 are similarly inserted between the terminals (electrodes 831 and 834) of pulse measurement phototransistor 32. This switch SW2 is closed when connector piece 80 is disconnected from connector 70, connecting the second capacitor C2 parallel to pulse measurement phototransistor 32, and is open when connector piece 80 is connected to connector 70.

Connector piece construction

The structure of connector piece 80 and connector 70 is described further below with reference to FIGS. 14A and 14B–FIG. 17.

FIGS. 14A and 14B are enlarged views showing the construction of the connector piece disposed at the end of the cable; FIG. 15 is an enlarged view of the connector on the device body; FIG. 16 is a vertical cross section showing the connector piece connected to the connector; and FIG. 17 is used to describe the circuit pattern and placement of the electrodes in the connector piece.

Referring to FIGS. 14A and 14B, a pair of projections 81 and 82 projecting downward is formed on both sides of the bottom 801 of connector piece 80. Four engaging members 811, 812, 821, and 822 (second group of engaging claws) project toward the inside at the bottoms of these projections 81 and 82.

Two operating pins 837 and 838 for switching a circuit blocking the effects of static electricity when cable 20 is connected to device body 10 are also provided on the bottom of connector piece 80. The ends of these operating pins 837 and 838 project from bottom 801 of connector piece 80 when connector piece 80 is removed from connector 70.

Six electrodes 831, 832, 833, 834, 835, 836 (second terminal group) are formed on the bottom 801 of connector piece 80, and an annular ridge member 841, 842, 843, 844, 845, and 846 is formed around each electrode. Connector piece 80 is thus fit down over connector 70 and then slid in the direction of arrow Q to mount connector piece 80 on connector 70 with electrodes 831–836 formed in two rows of electrodes 831, 833, and 833, and electrodes 834, 835, and 836 in this sliding direction (the direction of arrow Q). In addition, the electrodes 831–836 in each row are arranged at an angle offset in a direction intersecting the sliding direction (direction of arrow Q) of connector piece 80.

Connector configuration

As shown in FIG. 15, engaging parts 71, 72, 73, and 74 (first group of engaging claws) projecting to the outside are formed on connector 70. Therefore, if, after fitting connector piece 80 down over connector 70 such that projections 81 and 82 of connector piece 80 are positioned outside engaging parts 71, 72, 73, and 74 of connector 70, and engaging members 811 and 821 of connector piece 80 are positioned between engaging parts 71 and 72 and engaging parts 73 and 74, respectively, connector piece 80 is pushed towards connector 70 such that engaging members 811 and 821 pass between engaging parts 71 and 72 and engaging parts 73 and 74, respectively, (the first operation for connecting connector piece 80 to connector 70). Connector piece 80 is then slid in the direction of arrow Q (the mounting direction for connector piece 80, the direction from six o'clock to twelve o'clock of device body 10), engaging members 811, 821 become seated below engaging parts 71 and 73. Engaging members 812 and 822 are also seated below engaging parts 72 and 74.

As a result, engaging members 811, 821, 812, and 822 hold engaging parts 71, 72, 73, and 74 between engaging members 811, 821, 812, and 822 and bottom 801 of connector piece 80, and connector piece 80 can be easily and reliably connected to connector 70.

It should also be noted that terminals 751–756, like electrodes 831–836, are formed in two rows of terminals 751, 752, and 753 and terminals 754, 755, and 756 in the sliding direction of connector piece 80 (the direction of arrow Q). Each of these rows of terminals 751–756 is, like electrodes 831–836, arranged at an angle offset in a direction intersecting the sliding direction (direction of arrow Q) of connector piece 80. Therefore, when connector piece 80 is mounted on connector 70, the six terminals 751–756 are electrically connected to the six electrodes 831–836, respectively, and the measurement result from sensor unit 30 can be input to device body 10 through cable 20.

When connector piece 80 is disconnected from connector 70, connector piece 80 is slid in the opposite direction in the direction of arrow R. As a result, engaging members 811, 821 return to the positions between engaging parts 71 and 72 and engaging parts 73 and 74. Connector piece 80 can therefore be easily and reliably removed from connector 70 by simply lifting connector piece 80 up.

Engaging mechanism 700 is thus comprised such that connector piece 80 is engaged when connector piece 80 is slid across connector 70 in the direction of arrow Q, and this engaged state is released when connector piece 80 is slid from this state in the opposite direction (the direction of arrow R). The engaging mechanism thus comprised reliably engages even while using few parts.

When connector piece 80 is slid from six o'clock in the direction of twelve o'clock on connector 70, the force applied to device body 10 is applied in the direction whereby rotation of device body 10 is made difficult by turning stop 108. Because device body 10 therefore does not turn around the wrist even when connector piece 80 is mounted, mounting is simple.

Stopper mechanism construction

As will be known from FIG. 15, vertical faces 711, 721, 731, and 741 are formed on engaging parts 71–74 on the side in the direction of arrow Q. Therefore, if connector piece 80 is slid in the direction of arrow Q (second operation) when mounting connector piece 80 on connector 70, engaging members 811, 812, 821, and 822 respectively contact vertical faces 711, 721, 731, and 741, thus stopping connector piece 80 in the mounted position on connector 70. Vertical faces 711, 721, 731, and 741 therefore function as a first stopper for connector piece 80.

Conversely, when connector piece 80 is slid in the direction of arrow R for removal from connector 70, engaging members 811, 821 contact the backs of vertical faces 721 and 741 of engaging parts 72 and 74, thus stopping connector piece 80 in the original position on connector 70. The backs of vertical faces 721 and 741 thus function as second stoppers for connector piece 80.

Construction of terminals and electrodes

In connector 70, terminals 751–756 are each disposed inside holes 761, 762, 763, 764, 765, and 766 formed in connector 70. A cross section through where terminals 753 and 756, operating pin 838, and electrodes 833 and 836 are formed is shown in FIG. 16.

As shown in FIG. 16, connector piece 80 is constructed with cover member 806 covering outside case 805 in which circuit board 85 can be housed. Holes 863 and 866 are formed in cover member 806, and annular ridge members 843 and 846 are formed around the open lip at the bottom of the holes. Electrodes 833 and 836 are disposed inside holes 863 and 866. Electrode 833 is secured by screw 881, and electrode 836 is secured between circuit board 85 and cover member 806. A water-resistant packing 873 and 876 is also fit to electrodes 833 and 836. Electrodes 833 and 836 are electrically connected to the circuit pattern of circuit board 85 disposed inside connector piece 80. This electrical structure is the same for the electrodes other than electrodes 833 and 836, i.e., electrodes 831, 832, 834, and 835. Note that the wire of cable 20 is also electrically connected to the circuit pattern on circuit board 85 by soldering.

Click mechanism configuration

Connector 70 is constructed with the recess therein covered by cover member 706. Holes 763 and 766 are formed in cover member 706. Inside these holes 763 and 766 terminals 753 and 756 are disposed as retractable pins of which the tips project from holes 763 and 766. A coil spring 773 and 776 is disposed to the flange 783 and 786 formed at the base end of each terminal 753 and 756, and terminals 753 and 756 are pushed in the direction protruding from holes 763 and 766 by coil springs 773 and 776. However, because the outside diameter of flanges 783 and 786 is greater than the inside diameter of holes 763 and 766, terminals 753 and 756 will not slip out from holes 763 and 766. This terminal structure is the same for the terminals other than terminals 753 and 756, i.e., terminals 751, 752, 754, and 755.

Terminals 753 and 756 move over annular ridge members 843 and 846 of connector piece 80 while being pushed out by coil springs 773 and 776, and thus positively contact electrodes 833 and 836, because connector piece 80 is slid over connector 70 when connector piece 80 is mounted to connector 70. Because a click configuration is achieved by using annular ridge members 843 and 846, terminals 753 and 756, and coil springs 773 and 776 as is, connector piece 80 can be reliably connected to connector 70. Note that to achieve a click configuration of this type it is also possible to provide terminals using retractable pins on the connector piece 80 side, and provide the annular ridge members on the connector 70, opposite the arrangement of the present embodiment.

Switch mechanism configuration

Hole 868 is also formed in cover member 806 of connector piece 80, and operating pin 838 is disposed in this hole 868. This operating pin 838 is disposed to be retractable inside hole 868 with the tip thereof projecting from hole 868. A leaf spring type switch spring 88 is disposed to flange 898 formed on the base of operating pin 838. Switch spring 88 pushes operating pin 838 by means of the end 885 thereof in the direction projecting from hole 868. However, because the outside diameter of flange 898 is greater than the inside diameter of hole 868, operating pin 838 will not slip out from hole 868. Switch spring 88 is fastened with the base thereof held by screw 881 to the top of operating pin 838, and is thus electrically connected to electrode 833.

Referring to FIG. 17, end 885 of switch spring 88 comprises contact part 886 contacting the base of operating pin 838, and contact 887 formed on the part extending to the side therefrom. This contact 887 is electrically connected to circuit pattern 852 of circuit board 85. While not shown in the figure, this circuit pattern 852 is inserted between first capacitor C 1 and electrode 833.

Therefore, when connector piece 80 is not mounted on connector 70, operating pin 838 is pushed by switch spring 88 and the end projects from hole 868 as shown in FIG. 16, and in this state contact 887 of switch spring 88 is electrically connected to circuit pattern 852 of circuit board 85. More specifically, first switch SW1 closes in conjunction with the movement of operating pin 838 shown by the arrow in FIG. 13, and first capacitor Cl becomes electrically connected parallel to pulse measurement LED 31. As a result, even if a high potential charge caused by static electricity contacts electrodes 832 and 833, the charge is stored to first capacitor C1, and pulse measurement LED 31 is not damaged.

When connector piece 80 is mounted on connector 70, operating pin 838 moves in the direction into hole 868 as shown by the dot-dot-dash line in FIG. 16, and switch spring 88 is deformed as shown by the dot-dot-dash line. When switch spring 88 is thus deformed, contact 887 lifts from circuit pattern 852 of circuit board 85, and the electrical connection is broken. Specifically, when connector piece 80 is mounted to connector 70, first switch SW1 in FIG. 13 is open, and a circuit configuration capable of measuring the pulse is completed. In addition, even if a charge is stored to first capacitor Cl, the charge will not be discharged through electrodes 832 and 833 and terminals 752 and 753, and the circuits contained in connector 70 and device body 10 will not be damaged.

Furthermore, while this switch configuration is simple, it reliably tracks the mounting operation of connector piece 80 to connector 70.

It should also be noted that a switching mechanism of this configuration is also formed for pulse measurement phototransistor 32 as shown in FIG. 13. As will be known from FIG. 17, the configuration of this switching mechanism comprises an operating pin 837 and switch spring 89 similarly to the switching mechanism for pulse measurement LED 31, and further description thereof is therefore omitted below.

Connector cover configuration

FIGS. 18A and 18B show the configuration of connector cover 90, which is mounted to connector 70 in place of connector piece 80 when cable 20 and sensor unit 30 are removed from wrist-worn pulse wave measuring device 1A to use wrist-worn pulse wave measuring device 1A as a regular wristwatch.

Unlike connector piece 80, connector cover 90 does not require electrodes, a sensor circuit, and a cable. Connector cover 90 is, therefore, thinner overall and is shaped to not detract from the appearance when mounted to connector 70. However, the structure whereby connector cover 90 is mounted to connector 70 is the same as that of connector piece 80. Specifically, a pair of projections 91 and 92 projecting downward is formed on both sides of the bottom 901 of connector cover 90. Four engaging members 911, 912, 921, and 922 (second group of engaging claws) project toward the inside at the bottoms of these projections 91 and 92. Ridge members 941–946 forming a click mechanism with terminals 751–756 are formed on bottom 901 of connector cover 90 at the positions to which terminals 751–756 of connector 70 are disposed.

As with connector piece 80, when connector cover 90 is fit down over connector 70 such that engaging members 911 and 921 of connector cover 90 are positioned between engaging parts 71 and 72 and engaging parts 73 and 74, respectively, connector cover 90 is then pushed towards connector 70 such that engaging members 911 and 921 pass between engaging parts 71 and 72 and engaging parts 73 and 74, respectively. Connector cover 90 is then slid in the direction of arrow Q (the direction from six o'clock to twelve o'clock of device body 10) to mount connector piece 90 on connector 70, fitting and engaging members 911, 921 become seated below engaging parts 71 and 73. Engaging members 912 and 922 are also seated below engaging parts 72 and 74. As a result, engaging members 911, 921, 912, and 922 hold engaging parts 71, 72, 73, and 74 between engaging members 911, 921, 912, and 922 and bottom 901 of connector cover 90, and terminals 751–756 of connector 70 ride over ridge members 941–946, exhibiting a click force. Connector cover 90 is thus mounted on connector 70.

Use as a wristwatch

The operation of wrist-worn pulse wave measuring device 1A thus comprised is described briefly below with reference to FIG. 1 and FIGS. 7A–7C.

Referring first to FIGS. 2A–2B, when wrist-worn pulse wave measuring device 1A is used as a conventional wristwatch, device body 10 is held on the arm by means of wrist band 12 with cable 20 and sensor unit 30 disconnected from connector 70 of device body 10. At this time connector cover 90 shown in FIGS. 18A and 18B is mounted on connector 70, thus improving the appearance and protecting connector 70.

Operation in the pulse wave measurement mode

To measure the pulse rate while running using wrist-worn pulse wave measuring device 1A, connector piece 80 is mounted on connector 70 to connect cable 20 to device body 10. Device body 10 is then secured to the arm using wrist band 12 as shown in FIG. 2A. Sensor unit 30 (glass plate 304 of optical sensor unit 300) is then secured tightly to the finger by sensor securing band 40, and the user goes running.

When light is emitted toward the finger from pulse measurement LED 31 in this state as shown in FIG. 8, the light reaches the blood vessels, part of the light is absorbed by hemoglobin in the blood, and part is reflected. The light reflected from the finger (blood vessels) is detected by pulse measurement phototransistor 32, and the change in detected light quantity corresponds to the blood volume changes resulting from the blood pulse. Specifically, when the blood volume is great, the reflected light is weak; when the blood volume decreases, the reflected light becomes stronger. As a result, the pulse rate, etc., can be detected by monitoring the change in reflected light intensity with pulse measurement phototransistor 32. To accomplish such detection, the signal input from pulse measurement phototransistor 32 (sensor unit 30) is converted to a digital signal, and the pulse count is calculated by data processor 50 shown in FIG. 11 performing a frequency analysis or other operation on this digital signal. The pulse count obtained from this calculation is then displayed on liquid crystal display device 13. In short, wrist-worn pulse wave measuring device 1A functions as a pulse wave measuring device.

The pulse count and the time of the measurement are also output from pulse rate calculator 55 to data memory 56 at this time, and data processor 50 thus stores this data to data memory 56. When the lap time, split time, or other time data is also measured while running, this data is also stored to the data memory 56. If functions measuring the temperature or humidity are also built in to device body 10, this data is also stored to data memory 56.

The stored information can also be sequentially displayed to liquid crystal display device 13 after running is finished.

Referring again to FIG. 8, part of the light emitted from pulse measurement LED 31 travels through the finger and reaches the blood vessels as shown by arrow C, and the reflected light from the hemoglobin in the blood travels back to pulse measurement phototransistor 32 as shown by arrow D. The light quantity detected by this path is the "bioreflection."

Part of the light emitted from pulse measurement LED 31 is also reflected at the finger surface as shown by arrow E, and travels back to pulse measurement phototransistor 32. The light quantity detected by this path is the skin reflection.

Part of the light emitted from pulse measurement LED 31, and part of the light reflected from the blood vessels, is absorbed or diffused inside the finger as shown by arrows F and G, and does not reach pulse measurement phototransistor 32.

Sensor unit 30 uses pulse measurement LED 31 with an emissions wavelength range from 350 nm to 600 nm, and pulse measurement phototransistor 32 with a detection wavelength range from 300 nm to 600 nm, and the biological data is expressed based on the detection results in the overlapping wavelength range from approximately 350 nm to approximately 600 nm.

External light with a wavelength of 700 nm or less tends to not pass easily through the finger. Thus, even if the finger area not covered by sensor securing band 40 is exposed to external light, this light does not reach pulse measurement phototransistor 32 (pulse measurement photodetector) by travelling through the finger as an optical conductor as shown by arrow X in FIG. 8, and only light in the wavelength range not adversely affecting the detection results travels through the finger as an optical conductor. Because virtually all light below 300 nm is absorbed by the skin surface, the effective (real) wavelength detection range is 300 nm–700 nm even if the detection wavelength range is simply below 700 nm. It is therefore possible to suppress the effects of external light by covering the smallest necessary area and not covering a large part of the finger. If a small sensor unit 30 is used as described in this embodiment, the hand can be freely closed with sensor unit 30 worn at the base of the finger, and there is no interference with running. Furthermore, because cable 20 can be shortened if sensor unit 30 is worn at the base of the finger, cable 20 will not get in the way while running.

It is also known that the temperature drop at the base of the finger is relatively low even in cold weather. It is therefore possible to reliably measure the pulse rate even when running outdoors on a cold day because there is no significant drop in blood flow.

Wrist-worn pulse wave measuring device 1A according to the present embodiment is therefore suitable for measuring such things as the pulse count while running.

On the other hand, if an LED with an emissions peak near 880 nm and a silicon phototransistor are used, the detection wavelength range will range from 350 nm to 1200 nm. Detection errors caused by variations in the external light can therefore occur easily with a conventional optical system (detection device) because external light with a wavelength of 1 pm will easily pass through the finger as an optical conductor and reach the photodetector as shown by arrow Y in FIG. 8.

Moreover, the signal-to-noise (SIN) ratio of the pulse signal based on the blood volume change is high because the pulse wave information is obtained using light in the wavelength range from approximately 300 nm to approximately 700 nm. Regarding the relationship between optical wavelength and the optical absorption characteristics of various hemoglobins, the absorption coefficient of hemoglobin in the blood to light of a wavelength from 300 nm to 700 nm is great, and is several times to approximately 100 times the absorption coefficient with 880 nm wavelength light. The detection rate (SIN ratio) of the pulse based on the blood volume change is therefore high because the detection value varies with good sensitivity to the change in blood volume if light in the wavelength range for which the absorption coefficient is high (300 nm–700 nm) is used as the detected light based on the absorption characteristics of hemoglobin.

It should be noted that an element with an emissions wavelength ranging from 300 nm to 700 nm may be used for pulse measurement LED 31, and an element with a detection wavelength ranging below 700 nm may be used for pulse measurement phototransistor 32, if the objective is to obtain pulse information without the influence of external light. For example, a GaP type pulse measurement LED 31 having a primary emissions range from 540 nm to 570 nm, and a GaP type pulse measurement phototransistor 32 having a sensitivity range from 200 nm to nearly 700 nm, may also be used.

Operation in the data transmission mode

After wrist-worn pulse wave measuring device 1A is thus used to measure the pulse information, the data can be transmitted between wrist-worn pulse wave measuring device 1A and data processor 1B as shown in FIG. 1. This data transmission operation is executed according to a program stored, for example, in ROM. This program is described below with reference to FIGS. 19 and 20A–20C. FIG. 19 is a flow chart of the operation for transmitting data between wrist-worn pulse wave measuring device 1A and data processor 1B. FIGS. 20A–20C are signal waveform diagrams referenced in the description of this data transmission operation.

When data is transmitted between wrist-worn pulse wave measuring device 1A and data processor 1B, connector piece 80 of sensor unit 30 is first mounted on connector 70 (step ST11). As a result, the signals from sensor unit 30 are input to device body 10 through connector 70. Optical sensor unit 300 of sensor unit 30 is also connected to adapter 9. When wrist-worn pulse wave measuring device 1A and data processor 1B are thus connected, a pair of photocouplers enabling two-way data transmission is formed by pulse measurement LED 31, pulse measurement phototransistor 32, data transmission LED 7, and data transmission photodiode 8.

Signal discriminator 59A of wrist-worn pulse wave measuring device 1A then determines whether an identification code signal (optical signal) requesting data transmission has been received from data processor 1B (step ST12). If it is determined that this data transmission request signal has not been received, it is determined that optical sensor unit 300 is not connected to adapter 9 and the normal pulse measurement mode is active; pulse measurement is therefore started (step ST13). However, if it is determined (in step ST12) that this data transmission request signal has been received, wrist-worn pulse wave measuring device 1A enters the data transmission mode.

This identification code signal may be, as shown in FIG. 20A, 8 bits of data (D0–D7) transmitted after a signal indicating connector piece 80 is mounted to connector 70 has been input. If this 8-bit identification code signal is set, for example, to "5A" in hexadecimal code, the binary signal will be 01011010, i.e., a signal that cannot possibly be input while detecting the pulse wave. It is therefore possible for signal discriminator 59A to accurately determine whether the just-received signal is a pulse signal or a signal requesting data transmission. It should be noted that the identification code signal is not limited to 5Ah, and may be any signal that cannot possibly be input while detecting the pulse wave.

After the identification code signal is received by signal discriminator 59A in step ST12, an input/output identification code signal (an 8-bit optical signal of value 00h or FFh) is output from data processor 1B identifying whether data is to be input to wrist-worn pulse wave measuring device 1A or is to be output from wrist-worn pulse wave measuring device 1A.

Thus, if signal discriminator 59A determines in step ST14 that the input/output identification code signal (8-bit data code FFh) requesting data output from wrist-worn pulse wave measuring device 1A has been received as shown in FIG. 20B, data output controller 57A transmits the time change in the pulse count stored to data memory 56 as an optical signal from pulse measurement LED 31 to data processor 1B through pulse measurement phototransistor 32 (step ST15). When this optical signal is received by data transmission photodiode 8, the corresponding signal is input to data processor 1B. As a result, data processor 1B can store the time change in the pulse count and other information to the selected recording medium, and/or output the data to display 3 or printer 5, as necessary.

On the other hand, if signal discriminator 59A determines in step ST14 that the input/output identification code signal (8-bit data code 00h) requesting data input to wrist-worn pulse wave measuring device 1A has been received as shown in FIG. 20C, data input controller 57B begins the receiving process for signals transmitted from data processor 1B and used to adjust the clock or set the operating parameters of wrist-worn pulse wave measuring device 1A (step ST16). It is therefore possible to set the operating conditions of wrist-worn pulse wave measuring device 1A based on the data transmitted from data processor 1B.

As described above, it is possible by means of wrist-worn pulse wave measuring device 1A according to the present invention to display pulse information and other information on liquid crystal display device 13 of device body 10. It is also possible to transmit data to data processor 1B using data output controller 57A and pulse measurement LED 31. It is therefore also possible to batch display on data processor 1B data gathered while running, and to easily tabulate this data. Because it is also possible to receive data from data processor 1B using data input controller 57B and pulse measurement phototransistor 32, the conditions for various operations performed by wrist-worn pulse wave measuring device 1A can be input from data processor 1B to wrist-worn pulse wave measuring device 1A, and these settings can be stored to data memory 56. By thus being able to set operating conditions from data processor 1B, it is not necessary to provide many switches on wrist-worn pulse wave measuring device 1A.

The invention also creates no problems reducing the size and weight of wrist-worn pulse wave measuring device 1A because data can be transmitted using sensor unit 30, which was originally provided for the purpose of measuring pulse information.

Second embodiment

FIG. 21 is an illustration of the overall configuration of a pulse information processing apparatus according to an alternative embodiment of the present invention; FIG. 22 is a block diagram of the data processing circuit of the wrist-worn pulse wave measuring device used in the pulse information processing apparatus; and FIG. 23 is a diagram showing the circuit configuration of the connector of this wrist-worn pulse wave measuring device.

Note that the basic configuration of the wrist-worn pulse wave measuring device and pulse information processing apparatus according to the present embodiment is the same as that of the wrist-worn pulse wave measuring device and pulse information processing apparatus according to the previous embodiment. Identical references are therefore used for parts having the same function, and further description thereof is omitted below.

The sensor unit of the wrist-worn pulse wave measuring device is used for data transmissions in the pulse information processing apparatus of the previous embodiment. In the present embodiment, however, a data transmission connector piece 80D (connector member for transmitting data) that can be mounted on connector 70 of wrist-worn pulse wave measuring device 1A is provided on the data processor 1D (external device) side as shown in FIG. 21, and electrical signal data transmissions between wrist-worn pulse wave measuring device 1A and data processor 1D are accomplished using data transmission connector piece 80D and connector 70.

While there is no problem if a start-stop synchronization signal is output from wrist-worn pulse wave measuring device 1A, transmissions are incompatible with a personal computer type data processor 1D that directly processes a start-stop synchronization signal if wrist-worn pulse wave measuring device 1A outputs a clock synchronization signal. An interface unit 600 for converting between clock synchronization signals and start-stop synchronization signals is therefore provided at some point along data transmission cable 6, which leads from CPU 2 of data processor 1D. Interface unit 600 also performs voltage level conversion between the signals for wrist-worn pulse wave measuring device 1A and data processor 1D.

Note that the same structure used for pulse measurement connector piece 80 shown in FIGS. 14A and 14B can be used for data transmission connector piece 80D, and description thereof is thus omitted. The construction and operation of wrist-worn pulse wave measuring device 1A used as a pulse gauge is also identical to that of the wrist-worn pulse wave measuring device described above, and description thereof is thus omitted.

As shown in FIG. 22, data processor 50 in this embodiment also comprises data memory 56 for storing the pulse count and other pulse information obtained by pulse rate calculator 55, time data corresponding to this pulse information, and the lap time, split time, and other time data measured using the stopwatch feature of the wrist-worn pulse wave measuring device 1A while running.

Data processor 50 further comprises data input/output controller 57 for outputting the pulse information and time information stored to data memory 56 through connector 70 and data transmission connector piece 80D when wrist-worn pulse wave measuring device 1A is in the data transmission mode. Data input/output controller 57 also performs the processes storing data input through connector 70 and data transmission connector piece 80D to data memory 56.

Data processor 50 further comprises signal discriminator 59B for identifying the signal input through connector 70 and data transmission connector piece 80D. When the input signal from sensor unit 30 is a common pulse signal, signal discriminator 59B holds analog switch 58 open to enable pulse wave measurement. When signal discriminator 59B determines that the signal input through connector 70 and data transmission connector piece 80D is a signal from data processor 1D requesting the start of data transmission, signal discriminator 59B closes the open analog switch 58 to enable data transmission between wrist-worn pulse wave measuring device 1A and data processor 1D.

As shown in FIG. 22, it is therefore possible to switch between the pulse measurement mode and data transmission mode by means of signal discriminator 59B opening or closing analog switch 58.

The operation executed by wrist-worn pulse wave measuring device 1A to exchange data with data processor 1D is described below. This data transmission operation is also executed according to a program stored, for example, in ROM, and is described below with reference to FIGS. 24 and 25A–25C. FIG. 24 is a flow chart of the operation for transmitting data between wrist-worn pulse wave measuring device 1A and data processor ID. FIGS. 25A–25C are start-stop synchronization signal waveform diagrams referenced in the description of this data transmission operation.

When data is transmitted between wrist-worn pulse wave measuring device 1A and data processor ID, connector piece 80 of sensor unit 30 is first removed from connector 70, and data transmission connector piece 80D disposed to the end of data transmission cable 6 of data processor 1D is mounted to connector 70 in place of connector piece 80 (step ST21). Whichever connector piece is mounted to connector 70, electrode 835 and terminal 755 are electrically connected, and the potential of terminal 755 is the ON level.

Signal discriminator 59B of wrist-worn pulse wave measuring device 1A then determines whether an identification code signal requesting data transmission has been received from data processor 1D (step ST22). If it is determined that this data transmission request signal has not been received, it is determined that data transmission connector piece 80D is not connected to connector 70, and the normal pulse measurement mode is started on the determination that connector piece 80 is mounted (step ST23). However, if it is determined (in step ST22) that signal discriminator 59A received the data transmission request signal, wrist-worn pulse wave measuring device 1A enters the data transmission mode.

This identification code signal may be, as shown in FIG. 25A, 8 bits of data (D0–D7) transmitted from data processor 1D after a signal indicating connector piece 80 is mounted to connector 70 has been input. If this 8-bit identification code signal is set, for example, to "5A" in hexadecimal code, the binary signal will be 01011010, i.e., a signal that cannot possibly be input while detecting the pulse wave. It is therefore possible for signal discriminator 59B to accurately determine whether the just-received signal is a pulse signal or a signal requesting data transmission. It should be noted that the identification code signal is not limited to 5Ah, and may be any signal that cannot possibly be input while detecting the pulse wave.

After the identification code signal is received by signal discriminator 59B in step ST22, an input/output identification code signal (an 8-bit optical signal of value 00h or FFh) is output from data processor 1D identifying whether data is to be input to wrist-worn pulse wave measuring device 1A or is to be output from wrist-worn pulse wave measuring device 1A.

Thus, if signal discriminator 59B determines in step ST24 that the input/output identification code signal (8-bit data code FFh) requesting data output from wrist-worn pulse wave measuring device 1A has been received as shown in FIG. 25B, data input/output controller 57 transmits the time change in the pulse count stored to data memory 56 (step ST25). The voltage level of the signal output at this time is then converted by interface unit 600, and input to data processor 1D. As a result, data processor 1D can store the time change in the pulse count and other information to the selected recording medium, and/or output the data to display 3 or printer 5, as necessary.

On the other hand, if signal discriminator 59B determines in step ST24 that the input/output identification code signal (8-bit data code 00h) requesting data input to wrist-worn pulse wave measuring device 1A has been received as shown in FIG. 25C, data input/output controller 57 begins the receiving process for signals transmitted from data processor 1D and used to adjust the clock or set the operating parameters of wrist-worn pulse wave measuring device 1A (step ST26). It is therefore possible to set the operating conditions of wrist-worn pulse wave measuring device 1A based on the data transmitted from data processor I1. The voltage level of the signal output at this time is then converted by interface unit 600, and input to wrist-worn pulse wave measuring device 1A. As a result, data processor 1D can store the time change in the pulse count and other information to the selected recording medium, and/or output the data to display 3 or printer 5, as necessary.

It is therefore possible by means of the present embodiment as described above to transmit data between wrist-worn pulse wave measuring device 1A and data processor 1D using data input/output controller 57, connector 70, and data transmission connector piece 80D. It is also possible and convenient to batch process and display on data processor 1D data measured by wrist-worn pulse wave measuring device 1A. The operating conditions of wrist-worn pulse wave measuring device 1A can therefore also be set from data processor ID, and it is not necessary to provide many switches on wrist-worn pulse wave measuring device 1A.

The present invention thus creates no problems reducing the size and weight of wrist-worn pulse wave measuring device 1A because data can be transmitted using connector 70, which was originally provided for the purpose of mounting sensor unit 30.

While the invention has been described in conjunction with several specific embodiments, it is evident to those skilled in the art that many further alternatives, modifications and variations will be apparent in light of the foregoing description. Thus, the invention described herein is intended to embrace all such alternatives, modifications, applications and variations as may fall within the spirit and scope of the appended claims.

What is claimed is:

1. A wrist-worn pulse wave measuring device, comprising:
   a device body;
   a wrist band, coupled to said device body, for holding said device body on a wrist of a living body;
   a sensor unit
      (1) adapted to be mounted on the living body for measuring a pulse wave signal from the living body, and
      (2) adapted to be coupled to an external device for enabling communications between said device body and the external device;
   a connector removably coupling said sensor unit to the external device; and
   signal discrimination means for selectively
      enabling data communication between said device body and the external device when said sensor unit is coupled to the external device, and
      measuring the pulse wave signal by said device body from the living body when said sensor unit is mounted on the living body.

2. The wrist-worn pulse wave measuring device of claim 1,
   wherein a data transmission connector of the external device is coupled to said connector; and
   wherein data transmissions between said device body and the external device are through said connector and the data transmission connector.

3. The wrist-worn pulse wave measuring device of claim 1,
   wherein said device body comprises storage means for storing at least pulse information derived from the pulse wave signal measured by said sensor unit; and
   wherein said device body outputs the pulse information from said storage means to the external device via said connector.

4. The wrist-worn pulse wave measuring device of claim 1, wherein said sensor unit comprises a light emitter and a receptor adapted to face a surface of the living body.

5. The wrist-worn pulse wave measuring device of Claim 4,
   wherein said light emitter and the external device form a first photocoupler, and said receptor and the external device form a second photocoupler;
   wherein data transmissions between said device body and the external device are through said first and second photocouplers and said connector.

6. A pulse information processing apparatus, comprising:
   a data processor; and
   a wrist-worn pulse wave measuring device comprising
      a device body;
      a wrist band, coupled to said device body, for holding said device body on a wrist of a living body;
      a sensor unit
         (1) adapted to be mounted on the living body for measuring a pulse wave signal from the living body, and
         (2) adapted to be coupled to said data processor for enabling communications between said device body and with said data processor;
      a connector removably coupling said sensor unit to said data processor; and
      signal discrimination means for selectively
         enabling data communication between said device body and said data processor when said sensor unit is coupled to said data processor, and measuring the pulse wave signal by said device body from the living body when said sensor unit is mounted on the living body.

7. The wrist-worn pulse wave measuring device of claim 6, wherein said sensor unit comprises a light emitter and a receptor adapted to face a surface of the living body.

8. The wrist-worn pulse wave measuring device of claim 7, wherein said light emitter and the external device form a first photocoupler, and said receptor and said data processor form a second photocoupler;

wherein data transmissions between said device body and said data processor are through said first and second photocouplers and said connector.

9. The wrist-worn pulse wave measuring device of claim 6, wherein said data processor comprises a data transmission connector coupled to said connector; and wherein data transmissions between said device body and said data processor are through said data transmission connector and said connector.

10. The wrist-worn pulse wave measuring device of claim 6, wherein said device body comprises storage means for storing at least pulse information derived from the pulse wave signal measured by said sensor unit; and wherein said device body outputs the pulse information from said storage means to said data processor via said connector.

* * * * *